(12) United States Patent
Badylak et al.

(10) Patent No.: US 9,861,662 B2
(45) Date of Patent: Jan. 9, 2018

(54) BONE-DERIVED EXTRA CELLULAR MATRIX GEL

(71) Applicants: University of Pittsburgh—Of the Commonwealth System of Higher Education, Pittsburgh, PA (US); The University of Nottingham, Nottingham (GB)

(72) Inventors: Stephen F. Badylak, Pittsburgh, PA (US); Michael J. Sawkins, Nottingham (GB); Kevin M. Shakesheff, Nottingham (GB); Lisa J. White, Nottingham (GB)

(73) Assignees: University of Pittsburgh—Of the Commonwealth System of Higher Education, Pittsburgh, PA (US); The University of Nottingham, Nottingham (GB)

( * ) Notice: Subject to any disclaimer, the term of this patent is extended or adjusted under 35 U.S.C. 154(b) by 0 days.

(21) Appl. No.: 14/323,475

(22) Filed: Jul. 3, 2014

(65) Prior Publication Data
US 2015/0010510 A1 Jan. 8, 2015

Related U.S. Application Data

(60) Provisional application No. 61/842,507, filed on Jul. 3, 2013.

(51) Int. Cl.
*A61K 35/32* (2015.01)
*C12N 5/077* (2010.01)
*C12N 5/071* (2010.01)
*A61K 45/06* (2006.01)

(52) U.S. Cl.
CPC ............ *A61K 35/32* (2013.01); *A61K 45/06* (2013.01); *C12N 5/0654* (2013.01); *C12N 5/0697* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 4,563,350 A * | 1/1986 | Nathan | A61L 27/227 106/124.7 |
| 4,902,508 A | 2/1990 | Badylak et al. | |
| 4,956,178 A | 9/1990 | Badylak et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,554,389 A | 9/1996 | Badylak et al. | |
| 5,573,784 A | 11/1996 | Badylak et al. | |
| 5,645,860 A | 7/1997 | Knapp, Jr. et al. | |
| 5,711,969 A | 1/1998 | Patel et al. | |
| 5,753,267 A | 5/1998 | Badylak et al. | |
| 5,762,966 A | 6/1998 | Knapp, Jr. et al. | |
| 5,866,414 A | 2/1999 | Badylak et al. | |
| 6,099,567 A | 8/2000 | Badylak et al. | |
| 6,485,723 B1 | 11/2002 | Badylak et al. | |
| 6,576,265 B1 | 6/2003 | Spievack | |
| 6,579,538 B1 | 6/2003 | Spievack | |
| 6,696,270 B2 | 2/2004 | Badylak et al. | |
| 6,783,776 B2 | 8/2004 | Spievack | |
| 6,793,939 B2 | 9/2004 | Badylak | |
| 6,849,273 B2 | 2/2005 | Spievack | |
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 2005/0013872 A1* | 1/2005 | Freyman | A61K 35/28 424/549 |
| 2011/0195052 A1* | 8/2011 | Behnam | A61L 27/227 424/93.6 |

OTHER PUBLICATIONS

Russell et al., "Clinical Utility of Demineralized Bone Matrix for Osseous Defects, Arthrodesis, and Reconstruction: Impact of Processing Techniques and Study Methodology", Orthopedics 1999, vol. 22, pp. 524-531.*
Singelyn et al., "Naturally derived myocardial matrix as an injectable scaffold for cardiac tissue engineering", Biomaterials 2009, vol. 30, pp. 5409-5416.*
Acarturk et al.; "Commercially available demineralized bone matrix compositions to regenerate calvarial critical-sized bone defects"; Plast Reconstr Surg; 2006; pp. 862-73; vol. 118.
Badylak et al.; "Immune response to biologic scaffold materials"; Semin Immunol; 2008; pp. 109-16; vol. 20.
Beattie et al.; "Chemoattraction of progenitor cells by remodeling extracellular matrix scaffolds" Tissue Eng Part A; 2009; pp. 1119-1125; vol. 15.
Bostrom et al.; "An unexpected outcome during testing of commercially available demineralized bone graft materials: how safe are the nonallograft components?"; Spine; 2001; pp. 1425-1428; vol. 26; (Phila Pa 1976).
Brightman et al.; "Time-lapse confocal reflection microscopy of collagen fibrillogenesis and extracellular matrix assembly in vitro"; Biopolymers; 2000; pp. 222-234; vol. 54.
Brown et al.; "Macrophage phenotype and remodeling outcomes in response to biologic scaffolds with and without a cellular component"; Biomaterials; 2009; pp. 1482-1491; (also on p. 28, paragraph 77); vol. 30.
Cequiez-Sanchez et al.; "Dichloromethane as a Solvent for Lipid Extraction and Assessment of Lipid Classes and Fatty Acids from Samples of Different Natures"; J Agric Food Chem; 2008; p. 4297; vol. 56.
Crapo et al.; "An overview of tissue and whole organ decellularization processes"; Biomaterials; 2011; pp. 3233-3243; (p. 24, paragraph 72 and p. 26, paragraph 75); vol. 32.

(Continued)

*Primary Examiner* — Michelle F Paguio Frising
(74) *Attorney, Agent, or Firm* — The Webb Law Firm

(57) ABSTRACT

Methods of manufacturing a bone-derived extracellular matrix (bECM) product are provided. Also provided are bECM products and methods of using those products.

10 Claims, 10 Drawing Sheets

(56) References Cited

OTHER PUBLICATIONS

Daly et al.; "Effect of the a Gal epitope on the response to small intestinal submucosa extracellular matrix in a nonhuman primate model"; Tissue Eng Part A; 2009; pp. 3877-3888; vol. 15.
De Long et al.; "Bone grafts and bone graft substitutes in orthopaedic trauma surgery: a critical analysis"; J Bone Joint Surg; 2007; pp. 649-658; vol. 89.
Dequach et al.; "Injectable skeletal muscle matrix hydrogel promotes neovascularization and muscle cell infiltration in a hindlimb ischemia model"; Eur Cell Mater; 2012; pp. 400-412; vol. 23.
Freytes et al.; "Preparation and rheological characterization of a gel form of the porcine urinary bladder matrix"; Biomaterials; 2008; pp. 1630-1637; (also on p. 26, paragraph 74); vol. 29.
Galili; "The [alpha]-gal epitope and the anti-Gal antibody in xenotransplantation and in cancer immunotherapy"; Immunol Cell Biol; 2005; pp. 674-686; vol. 83.
Gilbert et al.; "Quantification of DNA in biologic scaffold materials"; J Surg Res; 2009; pp. 135-139; vol. 152.
Gruskin et al.; "Demineralized bone matrix in bone repair: history and use"; Adv Drug Deliv Rev; 2012; pp. 1063-1077; vol. 64.
Hadjipanayi E et al.; "Close dependence of fibroblast proliferation on collagen scaffold matrix stiffness"; Journal of Tissue Engineering and Regenerative Medicine; 2009; pp. 77-84; vol. 3.
Hong et al.; "Mechanical properties and in vivo behavior of a biodegradable synthetic polymer microfiber—extracellular matrix hydrogel biohybrid scaffold"; Biomaterials; 2011; pp. 3387-3394; vol. 32.
Keane et al.; "Consequences of ineffective decellularization of biologic scaffolds on the host response"; Biomaterials; 2012; pp. 1771-1781; vol. 33.
Lomas et al.; "An evaluation of the capacity of differently prepared demineralised bone matrices (DBM) and toxic residuals of ethylene oxide (EtOx) to provoke an inflammatory response in vitro"; Biomaterials; 2001; pp. 913-921; vol. 22.
Markel et al.; "Characterization of the inflammatory response to four commercial bone graft substitutes using a murine biocompatibility model" J Inflamm Res; 2012; pp. 3-8; vol. 5.
Peterson et al.; "Osteoinductivity of commercially available demineralized bone matrix preparations in a spine fusion model"; J Bone Joint Surg; 2004; pp. 2243-2250; vol. 86.
Pietrzak et al.; "BMP depletion occurs during prolonged acid demineralization of bone: characterization and implications for graft preparation"; Cell Tissue Bank; 2011; pp. 81-88; vol. 12.
Raeder et al.; Natural anti-galactose alpha 1,3 galactose antibodies delay, but do not prevent the acceptance of extracellular matrix xenografts; Transpl Immunol; 2002; pp. 15-24; vol. 10.
Reing et al.; "Degradation products of extracellular matrix affect cell migration and proliferation. Tissue Eng Part A"; 2009; pp. 605-614; vol. 15.
Reing et al.' The effects of processing methods upon mechanical and biologic properties of porcine dermal extracellular matrix scaffolds: Biomaterials; 2010; pp. 8626-8633; vol. 31.
Schenke-Layland et al.; "Impact of decellularization of xenogeneic tissue on extracellular matrix integrity for tissue engineering of heart valves"; J Struct Biol; 2003; pp. 201-208; vol. 143.
Stuart et al.; "Influence of chondroitin sulfate on collagen gel structure and mechanical properties at physiologically relevant levels"; Biopolymers; 2008; pp. 841-851; vol. 89.
Valentin et al.; "Functional skeletal muscle formation with a biologic scaffold"; Biomaterials; 2010; pp. 7475-7484; vol. 31.
Wang et al.; "A comparison of commercially available demineralized bone matrix for spinal fusion"; Eur Spine J; 2007; pp. 1233-1240; vol. 16.
Woessner; The determination of hydroxyproline in tissue and protein samples containing small proportions of this imino acid; Arch Biochem Biophys; 1961; pp. 440-447; vol. 93.
Wolf et al.; "A hydrogel derived from decellularized dermal extracellular matrix"; Biomaterials; 2012; pp. 7028-7038; vol. 33.
Wood; "The formation of fibrils from collagen solutions. 2. A mechanism of collagen-fibril formation"; Biochem J; 1960; pp. 598-605; vol. 75.
Wood et al.; "The formation of fibrils from collagen solutions. 1. The effect of experimental conditions: kinetic and electron-microscope studies"; Biochem J; 1960; pp. 588-598; vol. 75.
Yang et al.; "Favorable effects of the detergent and enzyme extraction method for preparing decellularized bovine pericardium scaffold for tissue engineered heart valves" J Biomed Mater Res B Appl Biomater; 2009; pp. 354-356; vol. 91.
Yang et al.; "Rheology and confocal reflectance microscopy as probes of mechanical properties and structure during collagen and collagen/hyaluronan self-assembly"; Biophys J; 2009; pp. 1566-1585; vol. 96.
Yazdi et al.; "Postmortem degradation of demineralized bone matrix osteoinductive potential: Effect of time and storage temperature"; Clin Orthop Relat Res; 1991; pp. 281-285; vol. 262.
Yoshida et al.; "Decellularization of bovine anterior cruciate ligament tissues minimizes immunogenic reactions to alpha-gal epitopes by human peripheral blood mononuclear cells"; Knee 2012; pp. 672-675; vol. 19.

\* cited by examiner

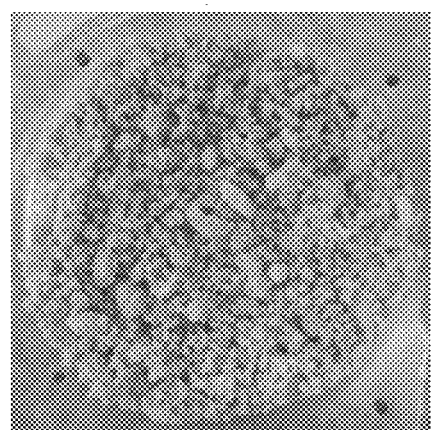
Fig. 1A
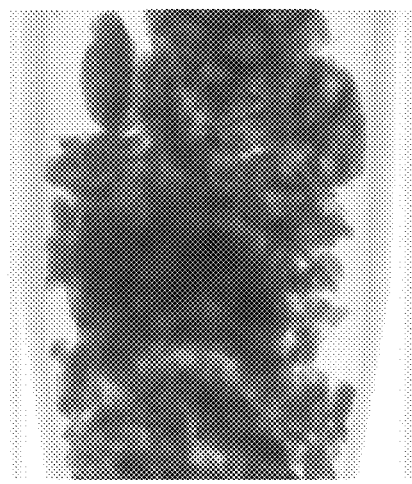 
Pre-demineralisation       Post 24 hrs demineralisation
Fig. 1B
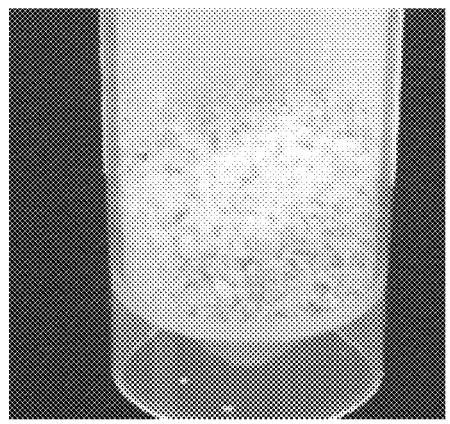 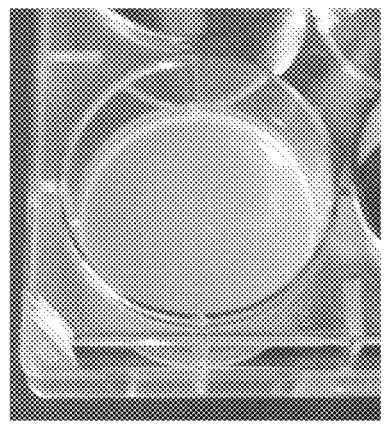
Fig 1C       Fig. 1D

BONE-DERIVED EXTRA CELLULAR MATRIX GEL

CROSS REFERENCE TO RELATED APPLICATIONS

This application claims the benefit of U.S. Provisional Application No. 61/842,507, filed Jul. 3, 2013, which is incorporated herein by reference in its entirety.

BACKGROUND OF THE INVENTION

1. Field of the Invention

Provided herein are bone-derived extracellular matrix compositions, along with methods of making and using the compositions.

2. Description of Related Art

The extracellular matrix (ECM) of mammalian tissues can be isolated, decellularized and utilized as a biological scaffold. Biological scaffolds derived from tissues such as the small intestine, urinary bladder or dermis have been shown to facilitate functional restoration of different tissues, including heart and vascular structures, esophagus and musculoskeletal tissues. The mechanisms by which constructive remodeling occur are well documented and include the recruitment of progenitor cells, promotion of cell migration and proliferation, regional angiogenesis and promotion of a favorable M2 macrophage phenotype at the interface of the host tissue and biological scaffold. Although these tissue-derived biological materials have been successfully used in non-homologous sites, recent studies have demonstrated "tissue specificity", with the occurrence of additional functions and complex tissue formation when biological scaffolds were derived from site-specific homologous tissues.

Musculo-skeletal conditions are the most common cause of severe long-term pain and physical disability worldwide, with more than 3 million musculoskeletal procedures performed annually in the USA. Degenerative disease, severe infection, trauma and the excision of tumors can result in large non-healing defects in bone and other integrated tissues. Current treatment options for bone have limited effectiveness. Although autologous bone grafts are considered to be the gold standard with the best clinical outcome, significant limitations include restricted availability of donor tissue and morbidity at the harvest site. Shortcomings of allografts comprise issues of processing, sterilization, disease transmission and potential immunogenic response, with high rates of fractures and complications, attributed to their limited ability to revascularize and remodel.

Bone graft substitutes, such as demineralized bone matrix (DBM), have been developed to overcome the limitations of both autografts and allografts. Osteoconductive DBM is produced by the acid extraction of the mineral content from allogeneic bone and contains growth factors, non-collagenous proteins and type I collagen. While the osteoinductive effect of DBM has been well-documented in animal studies, albeit with variability (Peterson B, et al. Osteoinductivity of commercially available demineralized bone matrix preparations in a spine fusion model. *J Bone Joint Surg* 2004; 86:2243-50 and Wang J C, et al. A comparison of commercially available demineralized bone matrix for spinal fusion. *Eur Spine J* 2007; 16:1233-40), there is a paucity of similar information for human clinical studies (De Long W G, et al. Bone grafts and bone graft substitutes in orthopaedic trauma surgery: a critical analysis. J Bone Joint Surg 2007; 89:649-58), despite a robust clinical demand for DBM products. Differences in the preparation and processing methods and donor age all have an impact on DBM properties and clinical performance (Gruskin E, et al. Demineralized bone matrix in bone repair: history and use. *Adv Drug Deliv Rev* 2012; 64:1063-77). The end product of the demineralization process is a DBM powder.

To facilitate handling, formulation and reliable delivery clinically these particles are usually incorporated in a carrier. For example, the most common clinical form of DBM is a moldable putty, which involves formulation with a biocompatible viscous carrier that provides a stable suspension of DBM powder particles (Id.). The viscous carriers are generally either water-soluble polymers, such as sodium hyaluronate or carboxymethylcellulose, or anhydrous water-miscible solvents, such as glycerol. Studies designed to test the effectiveness of various carriers on DBM efficacy are limited. One study reported nephrotoxicity (Bostrom M P, et al. An unexpected outcome during testing of commercially available demineralized bone graft materials: how safe are the nonallograft components? *Spine* (Phila Pa. 1976) 2001; 26:1425-8) amidst speculation regarding glycerol as a carrier. Differences in osteogenic activity have also been observed (Peterson B, et al. *J Bone Joint Surg* 2004; 86:2243-50; Wang J C, et al. *Eur Spine J* 2007; 16:1233-40; and Acarturk T O, et al. Commercially available demineralized bone matrix compositions to regenerate calvarial critical-sized bone defects. *Plast Reconstr Surg* 2006; 118: 862-73) which may be related to different carriers, the amount of DBM in the carrier and ability of the carrier to localize the DBM particulates to the bone defect site for a sufficient period of time to promote bone regeneration (Acarturk T O, et al. *Plast Reconstr Surg* 2006; 118:862-73). Additionally, a recent study characterized an inflammatory response to four commercial bone graft substitutes and found that the three DBM materials produced more inflammation than a synthetic hydroxyapatite compound. It was undetermined whether the DBM material or carrier provoked the inflammatory response (Markel D C, et al. Characterization of the inflammatory response to four commercial bone graft substitutes using a murine biocompatibility model. *J Inflamm Res* 2012; 5:13-8).

SUMMARY

The objectives of the methods described herein are to apply a stringent decellularization process to demineralized bone matrix (DBM), e.g., prepared from bovine bone, and to characterize the structure and composition of the resulting ECM materials and DBM itself. Additionally, we sought to produce a soluble form of DBM and ECM which could be induced to form a hydrogel. Current clinical delivery of DBM particles for treatment of bone defects requires incorporation of the particles within a carrier liquid. Differences in osteogenic activity, inflammation and nephrotoxicity have been reported with various carrier liquids. The use of hydrogel forms of DBM or ECM is expected to reduce the need for carrier liquids. DBM and ECM hydrogels exhibited sigmoidal gelation kinetics consistent with a nucleation and growth mechanism, with ECM hydrogels characterized by lower storage moduli than the DBM hydrogels. Enhanced proliferation of mouse primary calvarial cells was achieved on ECM hydrogels, compared with collagen type I and DBM hydrogels. These results show that DBM and ECM hydrogels have distinct structural, mechanical and biological properties and have the potential for clinical delivery without the need for carrier liquids.

According to a first embodiment of the invention, a method of preparing a bone-derived extracellular matrix (bECM) composition is provided. The method comprises: (a) demineralizing bone with an acid and/or a chelating agent to produce a demineralized bone matrix; (b) digesting the demineralized bone matrix with a protease to produce decellularized, demineralized bone matrix; and (c) digesting the decellularized, demineralized bone matrix with an acid protease to produce a solubilized, bone-derived ECM composition. According to one embodiment, the bone is comminuted prior to mineralization by any effective method, such as crushing, chopping, grinding, etc. In one embodiment, the bone is cancellous (trabecular spongy) bone. In one embodiment, the protease used to decellularize the demineralized bone matrix is trypsin. In one embodiment, the DNA content of the decellularized, demineralized bone matrix is less than 50 ng per mg of the decellularized, demineralized bone matrix. A number of reagents can be used to demineralize the bone. In one embodiment, the bone is demineralized in acid. In another embodiment, the bone is demineralized in a solution containing a chelating agent for calcium, such as ethylenediaminetetraacetic acid (EDTA). In one embodiment, a mineral/inorganic acid, such as hydrochloric acid, nitric acid, phosphoric acid, sulfuric acid, boric acid, hydrofluoric acid, hydrobromic acid, and perchloric acid is utilized for demineralization, at effective concentrations that do not substantially affect the utility of the final bECM product as described herein. In another embodiment, an organic acid, such as acetic acid, lactic acid, formic acid, citric acid, succinic acid, oxalic acid, or uric acid is utilized for demineralization, at effective concentrations that do not substantially affect the utility of the final bECM product as described herein. Combinations of inorganic and organic acids may be utilized for demineralization. In a further embodiment, EDTA and/or other chelating agent(s) are combined with an acid for decellularization purposes.

In one embodiment, demineralized, decellularized bone matrix is formed into a gel by digestion and solubilization with an acid protease, followed by neutralization and gelation at a suitable temperature. In one embodiment, the acid protease is pepsin. In one embodiment, the solubilized bone matrix is neutralized by adjusting the pH of the solubilized, decellularized, demineralized bone matrix to between 7 and 8 to produce a pre-gel. The neutralized pre-gel forms a gel at a temperature above the lower critical solution temperature (LCST) of the pre-gel, and preferably at a temperature ranging from at least 25° C. to 42° C.

In one embodiment, lipids are extracted from the demineralized, decellularized bone matrix, by extraction with an organic solvent, such as chloroform alone or in combination with a lower alcohol ($C_1$-$C_3$), such as methanol, ethanol or a propanol. In one embodiment, a subsequent wash with a lower alcohol, such as methanol, ethanol or a propanol, followed by a wash with an aqueous solvent can be used to wash organic solvent from the bone matrix. In any step provided herein the product of the step can be washed one or more times with an aqueous wash solution, such as water, PBS, cell culture medium or saline. Likewise, any product of any step can be frozen or dried, e.g., lyophilized between steps. Typically, the product of most, if not all steps is washed and optionally frozen.

Also provided herein is a solubilized, reverse gelling, bone-derived ECM composition. The composition comprises solubilized, decellularized bone-derived ECM that is a solution at a temperature lower than 20° C. and forms a gel at 37° C. The composition has a DNA content of less than 50 ng per mg of the gel. In one embodiment, the solubilized bone-derived ECM has a lower critical solution temperature in the range of from 20 to 35° C. According to another embodiment, the solubilized bone-derived ECM is produced by a method comprising the steps of: demineralizing bone with an acid to produce a demineralized bone matrix; decellularizing the demineralized bone matrix with a protease to produce a decellularized, demineralized bone matrix; and solubilizing the decellularized, demineralized bone matrix with an acid protease, thereby forming a solubilized bone-derived ECM composition. In a further embodiment, the method of producing the solubilize bone-derived ECM used to produce the composition further comprises the step of: neutralizing the pH of the solubilized bone-derived ECM composition to produce a pre-gel; and gelling the pre-gel at a temperature of at least 30° C. to produce a gel.

Also provided is a method of repairing an osteogenic defect in a patient comprising administering a bone-derived ECM gel prepared as described above and throughout this document to a patient in need of treatment for an osteogenic defect. In another embodiment, the bone-derived ECM composition further comprises at least one bioactive agent, for example a growth factor or a cell. For example the bone-derived ECM composition is seeded with cells prior to administration to the patient.

In yet another embodiment, a kit is provided comprising solubilized, decellularized, demineralized bone-derived ECM that, when neutralized, e.g., to a pH of between 7.0 and 8.0, is a solution at a temperature lower than 20 degrees centigrade and forms a gel at 37° C., the composition having a DNA content of less than 50 ng per mg of the gel. In one embodiment, the solubilized, decellularized, demineralized bone-derived ECM is dried (e.g., lyophilized).

In another embodiment, a method of culturing cells is provided, comprising contacting cells in cell culture medium with any embodiment, of a bone-derived extracellular matrix composition described herein.

BRIEF DESCRIPTION OF THE DRAWINGS

FIG. 1. Production of ECM hydrogel from bone. Bovine tibiae were processed to form (FIG. 1A) fragments and then subjected to mineral (FIG. 1B), lipid and cell removal procedures to produce (FIG. 1C) decellularized bone (bECM) prior to pepsin digestion and solubilization to form an ECM hydrogel (FIG. 1D).

In FIG. 2B, arrows indicate the presence of cell nuclei in demineralised tissue whilst dotted circle highlight occurrence of empty pits in decellularized tissue. The soluble collagen contents of the bDBM and bECM material were determined to be 0.93±0.06 and 0.92±0.06 mgs of collagen per mg of initial dry weight respectively.

DETAILED DESCRIPTION

Figure 2A:
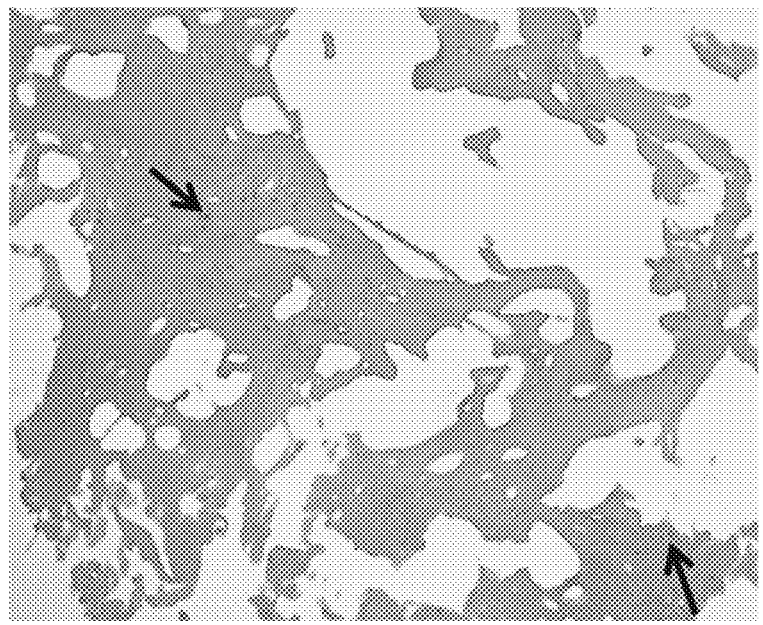
FIGS. 2A-2D. Decellularization was assessed by imaging and analysis of hematoxylin and eosin (H&E) stained sections of (FIG. 2A) bDBM (demineralized bone matrix) and (FIG. 2B) bECM and quantification of dsDNA content per mg dry weight measured with a Quant-iT™ PicoGreen® dsDNA assay kit for bone demineralized for 18 and 24 hours (FIG. 2C) and comparing bDBM and bECM prepared as described below (FIG. 2D).

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. "A" and "an" refer to one or more.

As used herein, the "treatment" or "treating" of a wound or defect means administration to a patient by any suitable dosage regimen and administration route of a composition with the object of achieving a desirable clinical/medical end-point, including attracting progenitor cells, healing a wound, correcting a defect, etc.

As used herein, the term "patient" refers to members of the animal kingdom including but not limited to mammals and human beings and is not limited to humans or animals in a doctor-patient or veterinarian-patient relationship. "A patient" refers to one or more patients such that a treatment effective in "a patient" refers to a treatment shown effective in one patient or a statistically significant number of patients in a population of patients. By "bone" or "bone material", it is meant a portion of a bone, a complete bone or more than one bones or portions thereof, and includes, without limitation, intact bone(s), crushed bone(s), ground bone(s), splintered bone(s) or comminuted bone(s), meaning the bone(s), or portion(s) thereof, is/are broken, cut or otherwise divided into smaller pieces. Bone comprises two types of osseous tissue, referred to as cancellous and cortical bone. Cancellous bone (substantia spongiosa ossium) is often referred to as trabecular bone or spongy bone, and is softer, weaker and less dense than cortical bone. Cancellous bone contains trabeculae and often marrow. Cortical bone is often referred to as compact bone, it forms the cortex of the bones and is much harder and denser than cancellous bone. In one embodiment, the bone material used to prepare the bDBM or bECM is cancellous, meaning it substantially or essentially comprises cancellous bone material. In another embodiment, the bone material used to prepare the bDBM or bECM is cortical, meaning it substantially or essentially comprises cancellous bone material. In yet another embodiment, the bone material used to prepare the bDBM or bECM comprises both cancellous and cortical bone material.

According to one embodiment of the invention, a method of preparing a bone-derived extracellular matrix material or composition is provided. The method results in a material that is unexpectedly efficient at growing cells and is a substantial improvement in the bone-repair field. The material, a gel, is useful without carriers typical to demineralized bone scaffolds, and not only removes the possibility for adverse reactions to such carriers, but provides a material that is superior to demineralized bone, collagen and tricalcium phosphate in its ability to support growth of bone cells, such as calvarial cells as shown below.

The method is performed on bone material, such as mammalian bone material, such as cow, pig, sheep, dog, cat or human bone material. In a preferred embodiment, the bone material comprises cancellous bone. In another embodiment, the bone material comprises a predominance of cancellous bone, such as 50% or more by weight, and preferably a greater percentage such as 75%, 80%, 90%, 95%, 99%, or greater percentage by weight of cancellous bone. In one embodiment, the bone material is cancellous bone, which is a bone preparation that removes cortical bone, and which is essentially cancellous bone with as much cortical bone removed as is practicable using acceptable protocols, recognizing that in most separation protocols, some cortical bone may remain in the preparation.

The bone material is not typically processed as an intact bone, but as bone fragments, particles, powders, etc. The bone can be comminuted, meaning the bone is divided into smaller pieces by any practical method, such as by grinding, milling, crushing, chopping, or the like, known to those of skill in the art. Comminuted bone has a higher surface area and can be more rapidly and completely demineralized, delipidized, and decellularized.

The bone is demineralized by treatment with an acid or chelating agent. In one embodiment, inorganic acid(s) or organic acid(s) are used to demineralize the bone. Non-limiting examples of inorganic acids include: hydrochloric acid, nitric acid, phosphoric acid, sulfuric acid, boric acid, hydrofluoric acid, hydrobromic acid, and perchloric acid. Non-limiting examples of organic acids include: acetic acid, lactic acid, formic acid, citric acid, succinic acid, oxalic acid, and uric acid. In one embodiment, combinations of two or more inorganic acids, organic acids or both inorganic and organic acids are employed to demineralize the bone. The concentration of acid(s) during demineralization, duration of demineralization, temperature of demineralization and other ingredients in the demineralization solution may vary so long as the desired degree of demineralization is accomplished without substantially damaging the remaining ECM materials for their intended purpose.

According to another embodiment, the bone is demineralized using a chelating agent, such as, for example and without limitation ethylenediaminetetraacetic acid (EDTA) and salts thereof, such as mono-, di-, tri- and tetra-sodium EDTA. Suitable concentration and pH ranges for EDTA and salts thereof are readily determinable, depending on the salt form of the EDTA and concentration ranges of from 1 mM to 1M, including increments thereof are expected to be useful, depending on the bone material used, and the demineralization conditions, such as pH, temperature, fineness of comminution of the bone, salt content, agitation, etc. Other examples of suitable chelating agents include analogs of EDTA, such as EGTA (ethylene glycol tetraacetic acid), nitrilotriacetic acid (NTA), pentasodium tripolyphosphate (STPP), and trisodium carboxymethyloxysuccinate (CMOS). In one embodiment, the chelating agent or salt thereof is combined with an acid, such as an inorganic acid or an organic acid to decellularize the bone, to the extent that the chelating agent is acid-soluble.

In some embodiments, the demineralized bone matrix are subject to a process to removed lipids, termed delipidization. Delipidization is accomplished by process(es) known to those of skill in the art, e.g., by organic extraction using organic solvent(s), so long as the process(es) do not detrimentally affect the characteristics of the final ECM product to any significance. Chloroform and dichloromethane (See, e.g., Cequiez-Sanchez E et al., Dichloromethane as a Solvent for Lipid Extraction and Assessment of Lipid Classes and Fatty Acids from Samples of Different Natures. *J Agric Food Chem* 2008, 56, 4297) are one non-limiting example of useful organic solvents for lipid extraction, and optionally can be combined together and/or with other organic solvents, such as lower ($C_1$-$C_3$) alcohols such as methanol, ethanol and propanol (isopropanol and n-propanol) and any combination thereof in any useful ratio. In some embodiments, delipidization is accomplished by incubating the demineralized bone matrix in chloroform, optionally in combination with methanol, for example a 1:1 ratio of chloroform and methanol. This incubation may proceed for as long as is required to remove lipids, for example for 1, 2, 3, 4, 5, 6, 7, 8, 12, 18 or 24 hours, or more, though as shown below, it has been found that a one-hour wash in an organic solvent (1:1 chloroform:methanol), followed by rinses with methanol and distilled water) yields a useful product. Following this incubation in chloroform and methanol, the demineralized bone matrix may be washed or rinsed, e.g., first with a lower alcohol, such as methanol and then with an aqueous solvent, such as water, saline or PBS, then optionally snap frozen and lyophilized. Demineralized bone matrix can be stored at a temperature below 0° C. until it is to be used. In some embodiments, storage at −20° C. or below is preferred.

As mentioned above, demineralized bone matrix is decellularized by incubation in one or more decellularization agents to remove cells from the demineralized product. In one embodiment, decellularization is performed using one or more enzymes, such as proteases. In embodiments, the demineralized bone matrix is incubated with a protease for up to 48 hours, preferably 24 hours. The protease may be provided at any suitable, effective concentration. Decellularization may be performed under suitable conditions known to those of skill in the art, for example at a temperature and atmospheric condition suitable for decellularization while maintaining the critical components of ECM. For example, and without limitation, decellularization can occur at between 20 and 37° C., with an atmospheric content of 1 to 10% $CO_2$, with or without agitation. In one embodiment, the protease is trypsin, provided, for example, at a concentration of 0.05%.

In further embodiments, the demineralized bone matrix is incubated with a chelating agent as well as the protease. In some embodiments, the chelating agent is EDTA. The chelating agent may be provided at any suitable concentration. In some embodiments, the chelating agent is provided at a concentration of 0.02%.

The decellularization process produces what may be referred to as decellularized, demineralized bone matrix, or decellularized matrix. This decellularized matrix may be washed, for example in an aqueous solvent such as water, saline or phosphate buffered saline (PBS) at any suitable concentration, to remove protease and, if present, chelating agent, as well as remaining cellular material(s). The aqueous solvent may be supplemented with additional agents, for example antibiotics. In non-limiting embodiments, the antibiotics are penicillin and/or streptomycin. This rinse may occur under any suitable conditions known to those of skill in the art, so long as functionality of the matrix in its ability to gel when the temperature is raised to approximately 37° C., and to support cell growth. For example, and without limitation, the matrix may be rinsed for 24 hours or more, at a temperature of less than 15° C., such as 4° C. Decellularized matrix can then be snap frozen and lyophilized to form a solid, and stored at a temperature below 0° C. until it is to be used. In some embodiments, storage at −20° C. or less may be preferred.

The ECM product described herein may be provided as a powder, or as a pre-gel or gel, such as a hydrogel. Pre-gel solutions are be obtained by digesting and solubilizing the decellularized matrix, which may be provided in powder form. Digestion and solubilization may be accomplished through use of an acid protease. The acid protease may be provided at any concentration useful for digesting the described bone ECM product. Those of skill in the art will appreciate that any suitable acid, at any suitable concentration, may be used to adjust the pH of the solution to allow for optimal activation of the protease and complete (to any practicable extent) solubilization of the ECM material. In some embodiments, the acid protease is pepsin, and the acid used is (e.g., 0.01 N) hydrochloric acid. Digestion and solubilization may occur under conditions known to those in the art to be suitable for these processes. In some embodiments, the solution is mixed constantly for 96 hours or more. Digested, solubilized bone-derived ECM pre-gel may be stored at a temperature below 0° C. until it is to be used. In some embodiments, storage at −20° C. may be preferred.

A characteristic of gels, such as hydrogels, that can be formed from the pre-gel solution provided according to the method described herein is that they are reverse-gelling. That is, the pre-gel solution exists as a solution at lower temperatures, such as room temperature, and gelation is induced at higher temperatures, such as physiologic temperatures. Pre-gel solution may be prepared for administration to a patient by neutralizing the pH of the solubilized bECM. For example, and without limitation, pH may be neutralized by adding a base, such as sodium hydroxide (NaOH) to the pre-gel solution in an amount effective to neutralize the pH of the pre-gel solution, that is, to provide a solution that has a pH between about 7 and about 8, preferably in the range of 7.2 and 7.8 and most preferably 7.4 or approximately or about 7.4. In a non-limiting embodiment, neutralization is accomplished using 0.1 N NaOH in 10×PBS, followed by dilution with 1×PBS to achieve a desired concentration of ECM. In one embodiment, neutralization of the solubilized bECM is accomplished at a temperature below the lower critical solution temperature (LCST) of the neutralized pre-gel to prevent gelation of the neutralized composition. In that embodiment, the temperature of the pre-gel is raised above the LCST (e.g., to above room temperature, such as at a temperature ranging from 25° C. to 42° C.) in order to initiate gelation. Typical LCST temperatures for the described compositions range between 15° C. and 30° C., such that the temperature of the neutralized pre-gel is maintained at least 5° C. or 10° C. below the LCST in order to maintain low viscosity of the solution until gelation is desired. In another embodiment, the pre-gel is neutralized at a temperature above the LCST of the product and is administered to a patient, or otherwise used or molded immediately. Those of skill in the art will appreciate that the temperature at which the gel is administered can affect gelation characteristics. In use, when administered in vivo to a patient, the neutralized pre-gel solution will be provided to an environment that is approximately 37° C. (body or physiologic temperature), where it will gel. The pre-gel can be placed in a mold and then placed into an incubator to raise the temperature to a gelation temperature.

The ECM materials and compositions disclosed herein can also be sterilized using art-recognized sterilization techniques prior to use in vivo, including glutaraldehyde tanning with glutaraldehyde, formaldehyde tanning at acidic pH, propylene oxide treatment, gas plasma sterilization, gamma radiation, electron beam and peracetic acid sterilization. The materials and compositions can be sterilized during the preparation of the pre-gel solution, or subsequent to the formation of the pre-gel solution but prior to administration to a patient, so long as function of the pre-gel is not substantially affected. In embodiments, a sterilization technique which does not significantly affect the characteristics of the ECM is used. Preferred sterilization techniques include exposing the graft to peracetic acid, 1-4 Mrads gamma irradiation, more preferably 1-2.5 Mrads of gamma irradiation, and gas plasma sterilization; peracetic acid sterilization being the most preferred method.

In certain embodiments, the pre-gel solution may be combined with one or more bioactive agents for delivery to a site of injury, or where repair is needed. As used herein, "bioactive agent" means any agent that has a biological effect on the patient. Bioactive agents can be admixed with the pre-gel solution, absorbed or adsorbed into the composition. Active agents that may be incorporated into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors.

In non-limiting embodiments, the bioactive agent is an immunosuppressant/immunomodulatory agent, for example glucocorticoids such as hydrocortisone, betamethasone, dexamethasone, flumethasone, isoflupredone, methylprednisolone, prednisone, prednisolone, and triamcinolone acetonide; antibodies; drugs acting on immunophilins, such as cyclosporine, zotarolimus, everolimus, tacrolimus and sirolimus (rapamycin), interferons, and TNF binding proteins.

In non-limiting embodiments, the bioactive agent is an antiangiogenic such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab and neovastat.

In non-limiting embodiments the bioactive agent is an antiproliferative such as sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP.

In non-limiting embodiments, the bioactive agent is an antibiotic or antimicrobial agent, such as, without limitation: acyclovir, ofloxacin, ampicillin, amphotericin B, atovaquone, azithromycin, ciprofloxacin, clarithromycin, clindamycin, clofazimine, dapsone, diclazuril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymyxin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

In non-limiting embodiments, the bioactive agent is a growth factor, such as basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotropin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany Techno-Gene Ltd., Rehovot, Israel; and Cell Sciences®, Canton, Mass. In certain embodiments, the growth factor is one or more useful growth factors useful in promoting bone regeneration/growth, such as platelet-derived growth factors (PDGFs), the transforming growth factor-beta (TGF-β) family, insulin-like growth factor (IGF-I) and the acidic and basic fibroblast growth factors (FGFs).

In non-limiting embodiments, the bioactive agent is a protein. In some embodiments, the protein is one or more that is useful for osteogenic purposes, such as bone morphogenetic proteins (BMPs) and osteogenic proteins (OPs).

In addition to the above, bioactive agents can include cells, such as genetically modified cells, stem cells, progenitor cells, and the like. Cells may be mixed with the pre-gel solution prior to gelation, or cells may be seeded on the gel once gelation has occurred, for uses in which the pre-gel solution is not provided to the patient in solution form. In one non-limiting embodiment, genetically modified cells are capable of expressing a therapeutic or bioactive substance, such as a growth factor. Cells can be modified by any useful method in the art. For example and without limitation, the therapeutic agent is a growth factor that is released by cells transfected with cDNA encoding for the growth factor. Therapeutics agents that can be released from cells include, without limitation, a neurotrophic factor, such as nerve growth factor, brain-derived neurotrophic factor, neurotrophin-3, neurotrophin-4, neurotrophin-5, and ciliary neurotrophic factor; a growth factor useful in promoting bone regeneration/growth, such as platelet-derived growth factors (PDGFs), the transforming growth factor-beta (TGF-β) family, insulin-like growth factor (IGF-I) and the acidic and basic fibroblast growth factors (FGFs); an anti-inflammatory cytokine; and an anti-inflammatory protein. The cells may be autologous, allogeneic, or xenogeneic.

The compositions described herein are useful for growing cells, tissues, organs in virtually any in vivo, ex vivo, or in vitro use, with particular focus on bone growth and/or repair. The material can be used as a substrate to facilitate the growth and differentiation of cells, whether in vivo or in vitro, into tissue, organ or body part precursors (e.g., anlagen), or even mature tissues or structures. The materials are useful in vitro as a cell growth medium to support the growth in culture of bone cells, bone cell precursor cells, stem cells, or virtually any other type of cells or cell-lines, including stem cells, progenitor cells or differentiated cells. The materials are expected to be useful in vivo as a cell growth scaffold for tissue growth for any useful purpose, including repair, replacement or augmentation of tissue in a patient in either humans or animals. For example, the materials are expected to be useful in repair and/or replacement of tissue lost or damaged during trauma or surgery, for example in loss of tissue after tumor removal. The materials are expected to be useful for cosmetic/restorative purposes. The materials described herein can be molded or contained within a structure to form desired shapes, such as, for bone repair or replacement. In one embodiment, the composition is employed as a cell-free scaffold, meaning the composition is applied at a location with no live cells. In another embodiment, the matrix is seeded with live cells, either, for example, by mixing the cells in the matrix prior to gelation, or by forming, e.g., by molding, the gel prior to seeding and placing cells on the formed gel in an ex vivo cell culture followed by implantation of the material in a patient. Useful cells include, e.g., bone cells and progenitors thereof, such as osteoblasts or cell mixtures containing osteoblasts, such as calvarial cell populations, bone marrow stem cells, bone marrow-derived mesenchymal or hematopoietic progenitor cells, or osteoblast precursors. Prior to implantation, the composition may be placed in a suitable tissue culture container with suitable medium and cells can be placed in contact with the matrix. The cells can be cultured for any suitable time period and then implanted in a patient. The matrix also can be dispersed in an aqueous solvent, such as water, saline (e.g., 0.9% saline) or PBS and injected, painted, sprayed or otherwise distributed on or in a bone of a patient to facilitate wound healing.

In one embodiment, the described neutralized pre-gel bECM composition, prepared by any embodiment described herein is placed in a mold that is shaped in any useful shape, for example in the shape of a bone or portion thereof, and is gelled at a temperature at or close to physiological temperature (approximately 37° C.), for example in a range of 35-42° C. In another embodiment, computer-aided processes also may be utilized to manufacture structures using the bECM material, such that the pre-gel is sprayed or otherwise deposited, for example by electrodeposition, in layers from a reservoir onto a "printed" structure. Other polymeric or active materials may be alternately deposited onto the nascent structure, producing a structure of varied layers. In one embodiment, the pre-gel is maintained at a temperature below the LCST of the bECM pre-gel material, such as at least 10° C. below the LCST, and the nascent structure is maintained at a temperature above the LCST of the bECM pre-gel material such that the composition gels upon deposition. Medically-acceptable adhesives can be used to assemble two or more molded/formed shapes of the bECM gel, and to attach the material to a site in a patient.

In its commercial use, the matrix described herein can be distributed in dried or hydrated form. In one embodiment, the matrix is distributed in gel (e.g., hydrated or hydrogel) form. In another embodiment, the matrix is distributed in dried form as a neutralized pre-gel as described above, that is hydrated for use. In one embodiment, the composition is hydrated at a temperature below the gelation temperature for the hydrated composition and which will form a gel once heated to above the gelation temperature as described above. For example, dried powder can be reconstituted by an end-user, or intermediary. It may be preferable to distribute the matrix as a kit comprising dried matrix and a suitable solution for rehydration of the sample. The matrix may be distributed as a powder, or as granules, depending on how finely the powder was comminuted during preparation.

In one embodiment, the matrix is distributed in a kit as a dry, e.g., lyophilized powder or granules in a container, along with a syringe or other reservoir that fits an opening on the container (that is, the container comprises a coupling for a syringe, such as a Luer lock, or a pierceable closure, or the like). The kit optionally comprises a hydrating solution, that is any suitable (e.g., sterile) aqueous solvent, such as water or saline), and which optionally is contained within the syringe during distribution. In use, the end-user injects the aqueous solvent into the container by either fitting the syringe onto the container or piercing the pierceable closure and then hydrates the matrix and fills the syringe with the hydrated matrix for injection as a means for implantation.

The following examples are provided for illustration.

Examples

The objectives of the present study were to apply a stringent decellularization process to DBM prepared from bovine bone and to characterize the structure and composition of the DBM and resulting ECM materials. We sought to produce a soluble form of the DBM and ECM materials which could be induced to polymerize into a gel. The rationale was to provide enhanced clinical utility of these materials without the inclusion of a carrier. The long-term objective of this work was to develop a gel form of DBM/ECM biological material that retains osteoconductivity and osteoinductivity. The present study describes the first steps towards this goal with characterization of the gelation kinetics, rheological properties and in vitro cytocompatibility of the gels.

Materials and Methods

1. Bone Preparation

Fresh bovine tibiae were harvested from cattle aged 12-24 months, slaughtered by an EU certified butcher. Bones were received in segmented form and were separated into cancellous and cortical groups, with the cancellous group used in this study. Bones were either used as received or stored at −20° C. in order to preserve their osteoinductive potential (Yazdi M, et al. Postmortem degradation of demineralized bone matrix osteoinductive potential. Effect of time and storage temperature. *Clin Orthop Relat Res* 1991; 262:281-5) and were processed using a modification of previously reported methods (Lomas R J, et al. An evaluation of the capacity of differently prepared demineralised bone matrices (DBM) and toxic residuals of ethylene oxide (EtOx) to provoke an inflammatory response in vitro. *Biomaterials* 2001; 22:913-21). Cancellous segments were cleaned of residual tissue and washed with phosphate-buffered saline (PBS) containing 0.1% w/v Gentamicin (Invitrogen, Paisley, UK). Washed segments were frozen in liquid nitrogen and sectioned to produce fragments no greater than 4×4×4 mm.

Fragments were washed in distilled water, immersed in liquid nitrogen and ground in a commercial coffee mill (Krups F203) (FIG. 1A).

2. Demineralization and Decellularization

Cancellous bone granules were demineralized using an adaptation of previously reported methods (Pietrzak W S, et al. BMP depletion occurs during prolonged acid demineralization of bone: characterization and implications for graft preparation. *Cell Tissue Bank* 2011; 12:81-88). In brief, the granules were demineralized under agitation in 0.5 N HCl (25 ml $g^{-1}$ bone) at room temperature for 24 h (FIG. 1B). Stirred beakers of bone granules and acid were agitated at 300 RPM to generate a small vortex; particles were suspended in motion in the acid and did not settle during the process. After demineralization the resultant material, referred to as bovine demineralized bone matrix (bDBM), was filter separated under vacuum from the acid and rinsed with distilled water. The lipid in the demineralized powder was then extracted with a 1:1 mixture of chloroform (Fisher Scientific, Loughborough, UK) and methanol (Fisher Scientific) for 1 h and then repeatedly rinsed, firstly in methanol and then distilled water. The bDBM was then snap frozen, lyophilized overnight and stored at −20° C. until required.

An enzymatic decellularization protocol, adapted from previously reported methods (Schenke-Layland K, et al. Impact of decellularization of xenogeneic tissue on extracellular matrix integrity for tissue engineering of heart valves. *J Struct Biol* 2003; 143:201-8), was applied. Briefly, lyophilized bDBM was rinsed with distilled water and decellularized in a solution of 0.05% trypsin (Sigma-Aldrich, Poole, UK) and 0.02% ethylenediamine tetraacetic acid (EDTA) (Sigma-Aldrich) at 37° C. and 5% $CO_2$ under continuous agitation for 24 h. The resultant material, referred to as bovine decellularized matrix (bECM) was rinsed in PBS supplemented with 1% w/v penicillin/streptomycin under continuous agitation for 24 h at 4° C. to remove residual cellular material. The bECM was then snap frozen, lyophilized overnight and stored at −20° C. until required (FIG. 1C).

3. Digestion and Solubilization

A previously reported pepsin digestion and solubilization technique was employed (Hong Y, et al. Mechanical properties and in vivo behavior of a biodegradable synthetic polymer microfiber-extracellular matrix hydrogel biohybrid scaffold. *Biomaterials* 2011; 32:3387-94). Lyophilized bDBM and bECM were separately added to 1 mg $ml^{-1}$ pepsin in 0.01 N HCl for a final concentration of 10 mg matrix per ml suspension, i.e. 1 g dry matrix was mixed with 100 mg pepsin in 100 ml of 0.01 N HCl. The suspension was mixed on a stirrer plate at room temperature for 96 h, until no visible pieces of matrix remained. The resultant bDBM and bECM digests were aliquoted and stored at −20° C. until required.

4. Assessment of Cellular Content

Representative samples of lyophilized bDBM and bECM were fixed in 10% neutral buffered formalin and embedded in 3% agarose gel prior to paraffin embedding. Sections were cut at 5-7 μm thickness and stained with hematoxylin and eosin (H&E) to identify the presence of any visible intact nuclei.

Quantification of DNA content was conducted by an adaptation of previously reported methods ((Gilbert T W, et al. Quantification of DNA in biologic scaffold materials. *J Surg Res* 2009; 152:135-9 and Keane T J, et al. Consequences of ineffective decellularization of biologic scaffolds on the host response. *Biomaterials* 2012; 33:1771-81)). DNA was extracted from pepsin digests of lyophilized bDBM and bECM (10 mg $ml^{-1}$ concentration) using 50:48:2 (vol. %) phenol/chloroform/isoamyl alcohol (Sigma-Aldrich, Poole, UK). DNA was precipitated from the aqueous phase at −20° C. by the addition of 0.1 volume of 3 M sodium acetate (pH 5.2) (Sigma-Aldrich, Poole, UK) and 2 volumes of ethanol and was then frozen. The frozen DNA was then centrifuged at 10,000 g for 10 min to form a DNA pellet. The pellet was washed with ethanol, dried at room temperature and resuspended in 1 ml of TE buffer.

The concentration of each extracted DNA sample was determined using a Quant-iT™ PicoGreen® dsDNA assay kit (Invitrogen, Paisley, UK) following the manufacturer's protocol. A standard curve was constructed by preparing samples of known DNA concentration from 0 to 1000 ng $ml^{-1}$. Extracted DNA samples were diluted to ensure their absorbencies fell within the linear region of the standard curve. Samples were read using a Tecan Infinite M200 plate reader (Tecan UK, Reading, UK).

5. Assessment of Collagen Content

The hydroxyproline content of pepsin digests of bDBM and bECM was determined by hydrolysing with concentrated HCl (1 ml of each solution) at 120° C. overnight. Samples were incubated uncapped at 90° C. until dry and then 4 ml of 0.25 M sodium phosphate buffer (pH 6.5) (Sigma-Aldrich, Poole, UK) was added to each sample. Blank pepsin solution was hydrolyzed and used as a control and diluent for the assay. 50 μl of each sample was reacted with 50 μl of chloramine T solution (Sigma-Aldrich, Poole, UK) and allowed to oxidize at room temperature for 20 min. The samples were then mixed with 50 μl of p-dimethylaminobenzaldehyde (p-DAB) (Ehrlich's reagent, Sigma-Aldrich, Poole, UK) and incubated at 60° C. for 30 min. A standard curve was constructed by preparing samples of known hydroxyproline concentrations from 0 to 30 μg $ml^{-1}$. The colorimetric change at an absorbance of 540 nm was detected using a Tecan Infinite M200 plate reader (Tecan UK, Reading, UK). The total collagen content of the digests was determined using the relationship that hydroxyproline forms 14.3% of total collagen (see, e.g., Woessner J F. The determination of hydroxyproline in tissue and protein samples containing small proportions of this imino acid. *Arch Biochem Biophys* 1961; 93:440-7).

6. Gelation

Rat tail collagen type I, bDBM and bECM gels were formed using a previously described method (Freytes D O, et al. Preparation and rheological characterization of a gel form of the porcine urinary bladder matrix. *Biomaterials* 2008; 29:1630-7 and Wolf M T, et al. A hydrogel derived from decellularized dermal extracellular matrix. *Biomaterials* 2012; 33:7028-38). Briefly, gelation was induced by neutralizing the salt concentration and pH of the pepsin digests or collagen solution at 4° C. followed by warming to 37° C. Neutralization of the required digest volume occurred by addition of one tenth of the digest volume of 0.1 N NaOH, one ninth of the digest volume of 10×PBS and by then diluting to the desired final ECM concentration with 1×PBS on ice. Gelation of this pre-gel solution occurred after 1 h at 37° C. (FIG. 1D). Concentrations of 3 and 6 mg $ml^{-1}$ bECM, bDBM and collagen were prepared. Turbidimetric gelation kinetics of collagen type I (Coll I), bDBM and bECM hydrogels were determined spectrophotometrically as previously described (Freytes D O, et al. *Biomaterials* 2008; 29:1630-7). Pre-gel solutions were kept at 4° C. and transferred to cold 96-well plates (100 μl). The plates were placed in a pre-warmed (37° C.) Tecan Infinite M200 plate reader and the turbidity of each well measured at 405 nm every 3 min for 1.5 h.

Absorbance values for each well were recorded; six individual (n=6) measurements of each hydrogel type and concentration were performed and the results averaged. These readings were then scaled from 0 (at time 0) to 1 (at maximum absorbance) to provide a normalized absorbance (NA) as shown in Eq. (1).

$$NA = \frac{A - A_0}{A_{max} - A_0} \quad (1)$$

where A is the absorbance at a given time, $A_0$ is the initial absorbance and $A_{max}$ is the maximum absorbance. The lag time (tlag) was defined as the intercept of the linear region of the gelation curve with 0% absorbance.

7. Rheological Characteristics

The rheological characteristics of bECM, bDBM and collagen type I hydrogels were determined using a Physica MCR 301 rheometer (Anton Paar, Hertford, UK). Pre-gel solutions at 4° C. were placed between 50 mm parallel plates separated by a 0.2 mm gap. The plates were pre-cooled in a humidified chamber to 4° C. and were then warmed to 37° C. during the first 75 s of each measurement run. Initially a 60 min time course experiment was performed during which the samples were subjected to an oscillatory strain of 1% at a constant angular frequency of 1 rad s$^{-1}$ with readings taken every 30 s. Immediately following this the samples were subjected to an amplitude sweep covering the range 0.1-200% strain at the same constant angular frequency.

8. Gel Morphology

Surface morphology of the bDBM, bECM and collagen type I hydrogels was examined by scanning electron microscopy (SEM). Gel specimens (400 µl per well) were fixed in 1 ml of 3% glutaraldehyde and then rinsed in PBS, followed by dehydration through a graded series of ethanol (30-100%). Subsequently the hydrogels were critically point dried in a Samdri pvt-3 critical point dryer (Tousimis, Rockville, Md.). The samples were then attached to aluminium mounting stubs and sputter coated with platinum using a Polaron SC7640 (Quorum Technologies, Ashford, UK) sputter coater at a voltage of 2.2 kV and plasma current of 15 mA for 90 s. Hydrogels were then examined using a Phillips XL30 FEG SEM (FEI, Eindhoven, The Netherlands) and images were obtained at 8000× and 16,000× magnification.

9. In Vitro Cell Proliferation

Mouse primary calvarial cells (mPCs), an osteogenic population of cells comprised predominantly of osteoblasts, were obtained from 1- to 3-day-old mouse calvaria by sequential enzymatic digestion. Briefly, the calvaria were dissected from CD1 neonates and digested using a solution of 1.4 mg ml$^{-1}$ collagenase type IA and 0.5 mg ml$^{-1}$ trypsin II S (Sigma-Aldrich, Poole, UK). Cells released in the first two populations (10 min each digestion) were discarded and the population of cells from the next three digestions (20 min each digestion) were plated in tissue culture flasks at a density of 6.6×10$^3$ cells cm$^{-2}$. All digestions were performed on rollers set to 30 RPM at 37° C. Cells were cultured in a-minimal essential medium (Lonza, Slough, UK) containing 10% fetal calf serum (FCS) and 2 mM L-glutamine (Sigma-Aldrich, Poole, UK) and 100 U ml$^{-1}$ penicillin and 100 µg ml$^{-1}$ streptomycin (Invitrogen, Paisley, UK). In vitro cell proliferation on the surface of 3 and 6 mg ml$^{-1}$ bECM, bDBM and collagen type I hydrogels was characterized using the CellTiter 96® Aqueous Non-radioactive MTS colorimetric assay (Promega, Southampton, UK). Briefly, pre-gel solutions kept at 4° C. and transferred to cold 96-well plates (100 µl). Once the hydrogels had formed (1 h at 37° C.) mPCs were added to the surface of the gels and cultured for 48-72 h. Proliferation was assessed following the manufacturer's instructions; the CellTiter 96® MTS solution is bioreduced by cells to a formazan product, soluble in tissue culture medium. Briefly, 20 µl of CellTiter 96® AQueous One Solution was added to each well, incubated for 3 h and the absorbance of the formazan product at 490 nm measured directly using a Tecan Infinite M200 plate reader. The conversion of MTS to the aqueous soluble formazan product is accomplished by dehydrogenase enzymes found in metabolically active cells. Thus the quantity of formazan product measured as the 490 nm absorbance is directly proportional to the number of living cells in culture. The background absorbance of each distinct hydrogel type and concentration was subtracted from the absorbance of mPCs on the corresponding hydrogel to provide a normalized absorbance. All conditions were assessed in sextuplicate.

10. Statistical Analysis

All statistical analyses were performed using GraphPad Instat (Graph Pad Software Inc., La Jolla, Calif.). All values are reported as means±standard deviation. In vitro cell proliferation values were tested for normality and statistically compared using a Tukey-Kramer multiple comparisons test. Significance for all statistical analyses was defined as p<0.001.

Results

1. Preparation of ECM Hydrogel from Bone

Fresh bovine tibiae were processed into a fragmented form and demineralized using acid extraction to remove the mineral content. Lipid removal was achieved with chloroform/methanol, and an enzymatic decellularization procedure was applied to the demineralized bone matrix (bDBM) to produce decellularized matrix material (bECM) (FIG. 1). The bDBM and bECM materials were digested and solubilized with pepsin and hydrogels were successfully prepared from both bDBM and bECM at concentrations of 3 and 6 mg ml$^{-1}$. The higher ECM/DBM concentration hydrogels (6 mg ml$^{-1}$) had a more rigid structure compared with the lower concentration (3 mg ml$^{-1}$) hydrogels.

2. Cellular and Collagen Content of Demineralized and Decellularized Material

Figure 2B:
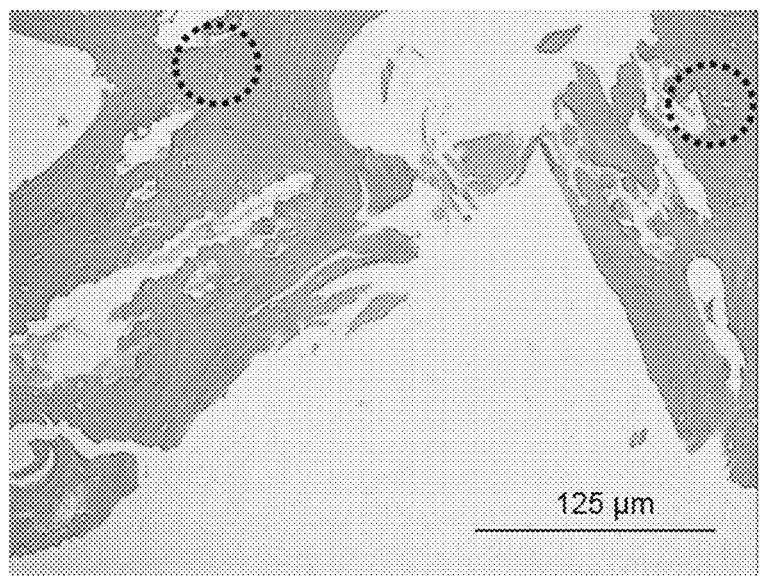
Figure 2C:
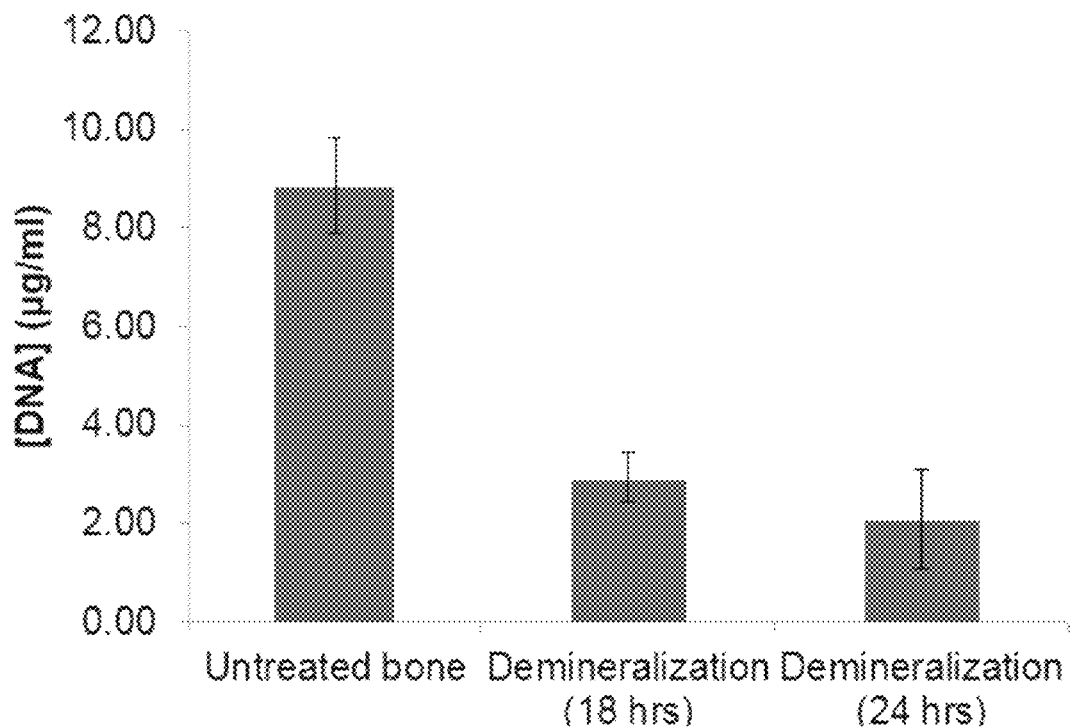
Figure 2D:
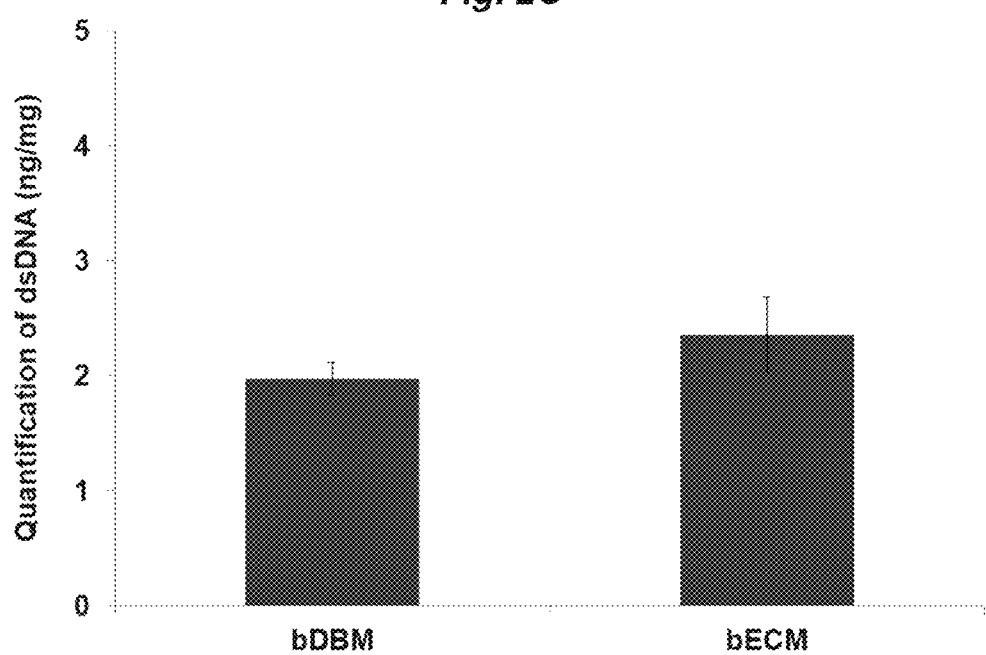

Determination of effective decellularization was based upon established criteria (Reing J E, et al. The effects of processing methods upon mechanical and biologic properties of porcine dermal extracellular matrix scaffolds. *Biomaterials* 2010; 31:8626-33 and Crapo P M, et al. An overview of tissue and whole organ decellularization processes. *Biomaterials* 2011; 32:3233-43), specifically: (i) removal of nuclei as observed by imaging and analysis of H&E and/or DAPI stained sections; (ii) samples should possess <50 ng double stranded DNA (dsDNA) per mg initial dry weight (e.g., by Pico green, for example using the Quant-iT™ PicoGreen® dsDNA Assay Kit, as described herein). H&E sections clearly showed that decellularization had removed all cell nuclei (FIG. 2B), but some cell nuclei appeared to be present in demineralized sections (FIG. 2A). Quantification of dsDNA content showed that this was considerably lower than the 50 ng threshold in demineralized bone, and in both bDBM and bECM (FIGS. 2C and 2D).

3. Turbidimetric Gelation Kinetics

Figure 3A:
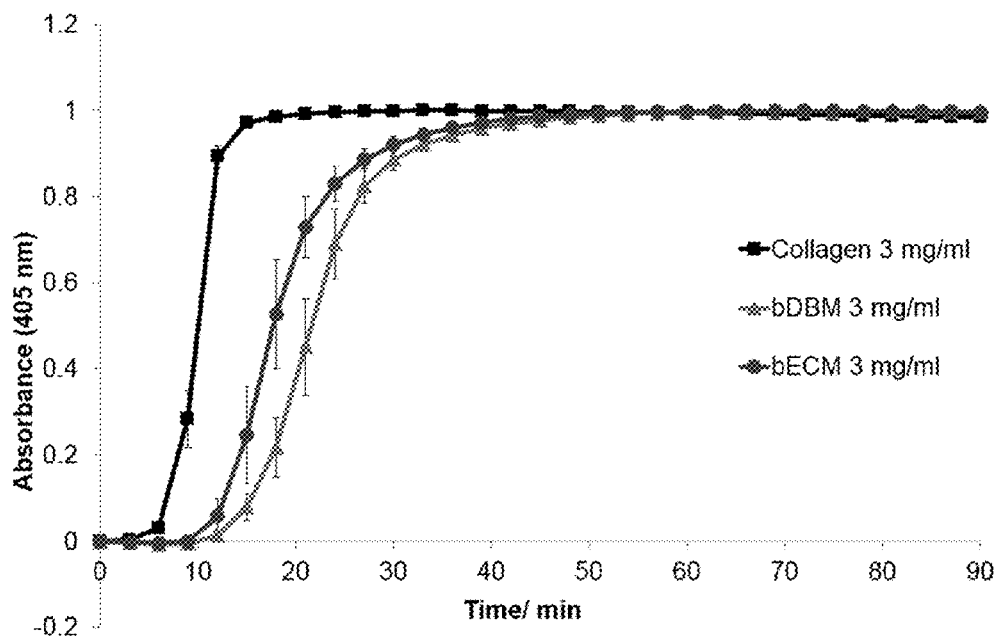
FIG. 3. Turbidimetric gelation kinetics of bECM and bDBM hydrogels compared with collagen at (A) 3 mg ml$^{-1}$ and (B) 6 mg ml$^{-1}$ concentrations. Pre-gel solutions were neutralized and added to the wells of a 96-well plate at 37° C. to induce gelation. The absorbance at 405 nm was measured at 3 min intervals and normalized between 0 (the initial absorbance) and 1 (the maximum absorbance). Data represent means±standard deviation for n=6.
Figure 3B:
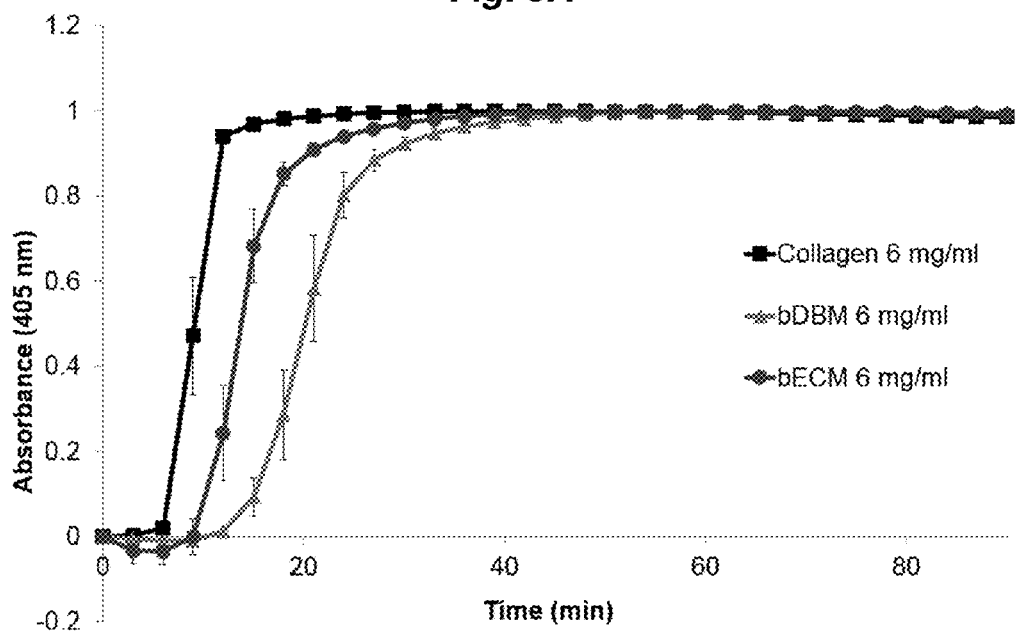

The turbidimetric gelation kinetics of bDBM and bECM hydrogels were characterized spectrophotometrically and compared with the same concentration (3 and 6 mg ml$^{-1}$)

collagen type I hydrogels. The turbidimetric gelation kinetics for all materials and concentrations showed a sigmoidal shape (FIGS. 3A and 3B) with hydrogel formation occurring after a lag period ($t_{lag}$). At both concentrations the collagen type I hydrogel had a shorter $t_{lag}$ than the bECM hydrogel, which had a shorter $t_{lag}$ than the bDBM hydrogel. Gelation kinetics appeared to be independent of concentration. The time course shows that collagen has a very rapid gelation whereas with bDBM and bECM that there may be two-phase gelation kinetics due to the presence of GAGs.

4. bDBM, bECM and Collagen Type I Hydrogel Rheology

The rheological characteristics of the bDBM and bECM hydrogels were determined using a parallel plate rheometer and compared with the same concentration (3 and 6 mg ml$^{-1}$) collagen type I hydrogels. In each case the storage (G') and loss (G") moduli of the hydrogels increased after the pepsin digests (or pre-gel collagen type I solutions) were neutralized and the temperature was increased from 4° C. to 37° C. Solid-like behavior was confirmed as the storage moduli were greater than the loss moduli by a factor of approximately 10 for the bECM and bDBM hydrogels and a factor of approximately 20 for the collagen type I hydrogels (FIGS. 4A and 4B).

Figure 4A:
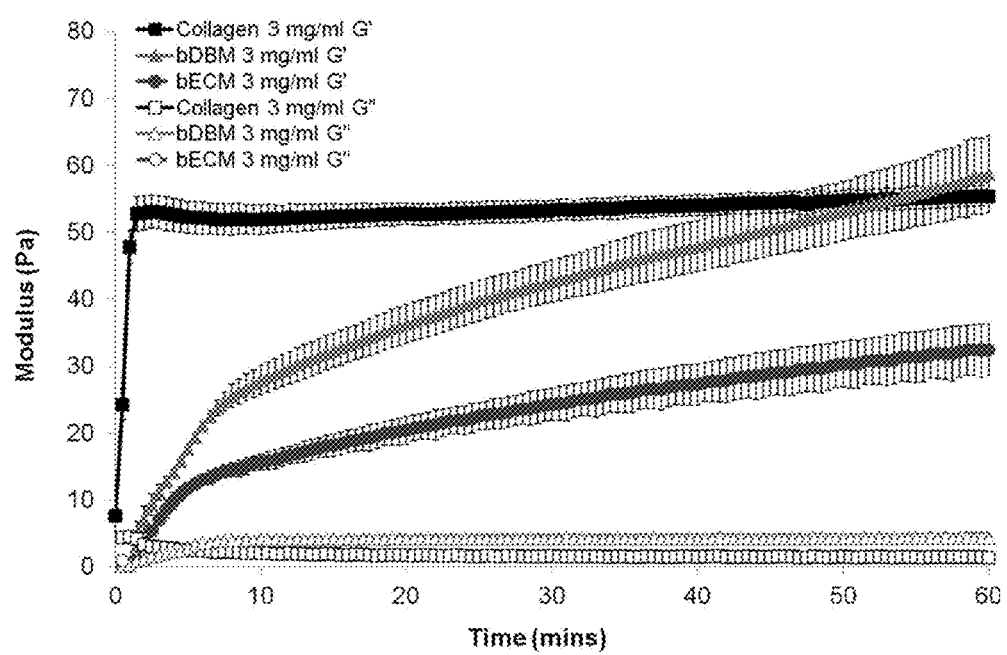
FIGS. 4A and 4B. Rheological characterization of bECM, bDBM and collagen type I 3 mg ml$^{-1}$ (FIG. 4A) and 6 mg ml$^{-1}$ (FIG. 4B) hydrogels. The gelation kinetics were determined by monitoring changes in the storage modulus (G') and loss modulus (G") after inducing gelation. Data represent means±standard deviation for n=6.
Figure 4B:
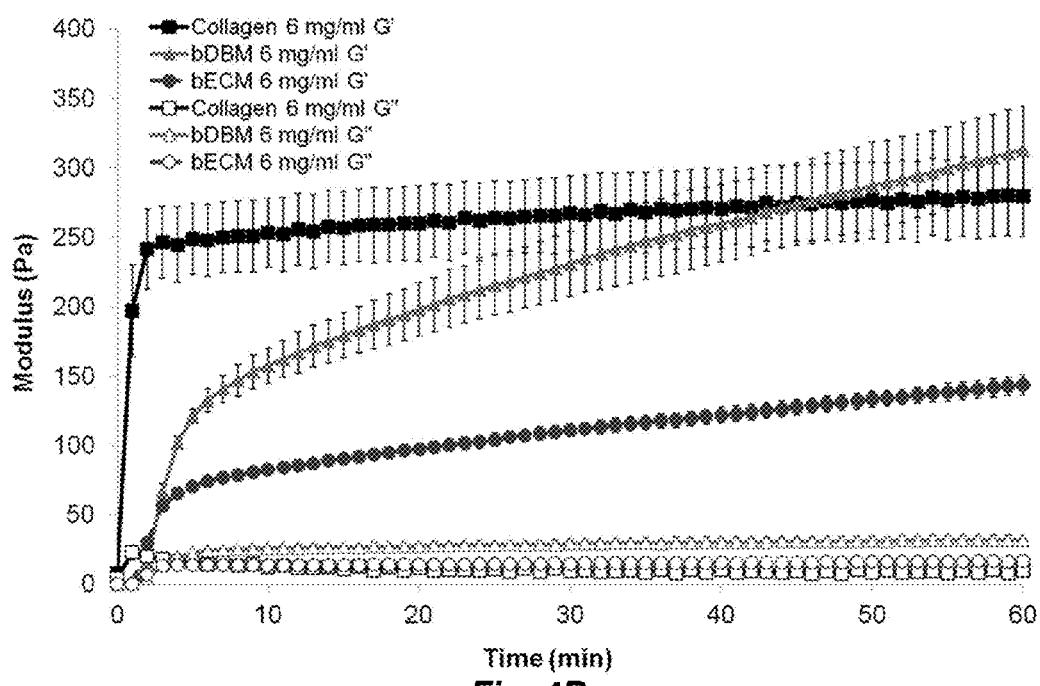
Figure 5A:
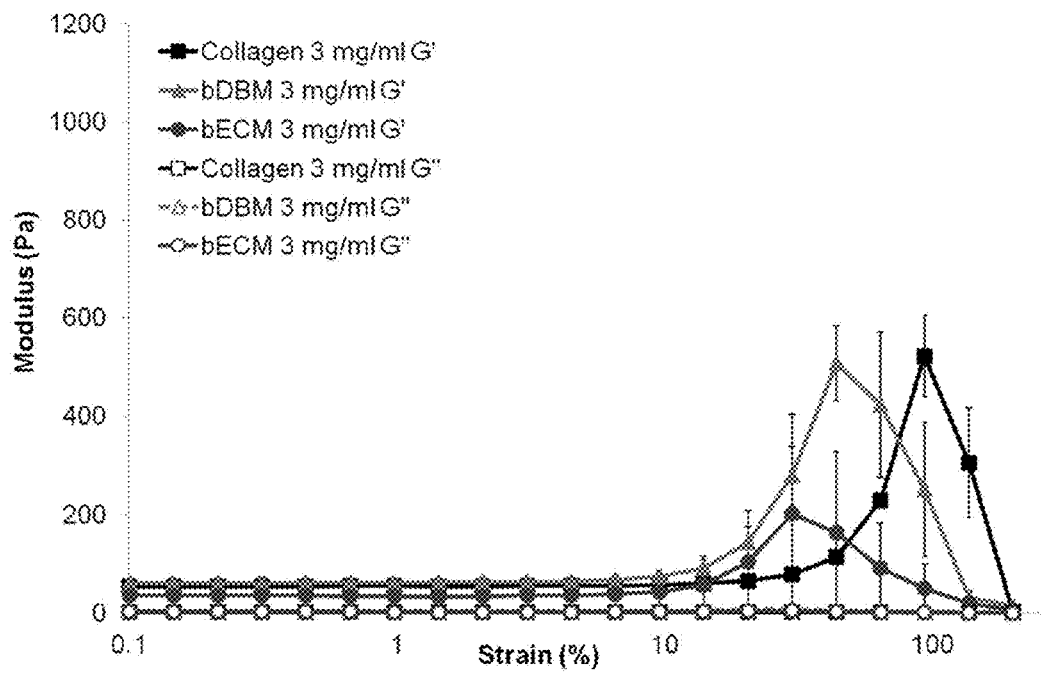
FIG. 5. Amplitude sweep of bECM, bDBM and collagen type I 3 mg ml$^{-1}$ (FIG. 5A) and 6 mg ml$^{-1}$ (FIG. 5B) hydrogels. The storage modulus (G') and loss modulus (G") were monitored when hydrogels were subjected to an amplitude sweep of 0.1-200% strain at a constant angular frequency. Data represent means±standard deviation for n=6.
Figure 5B:
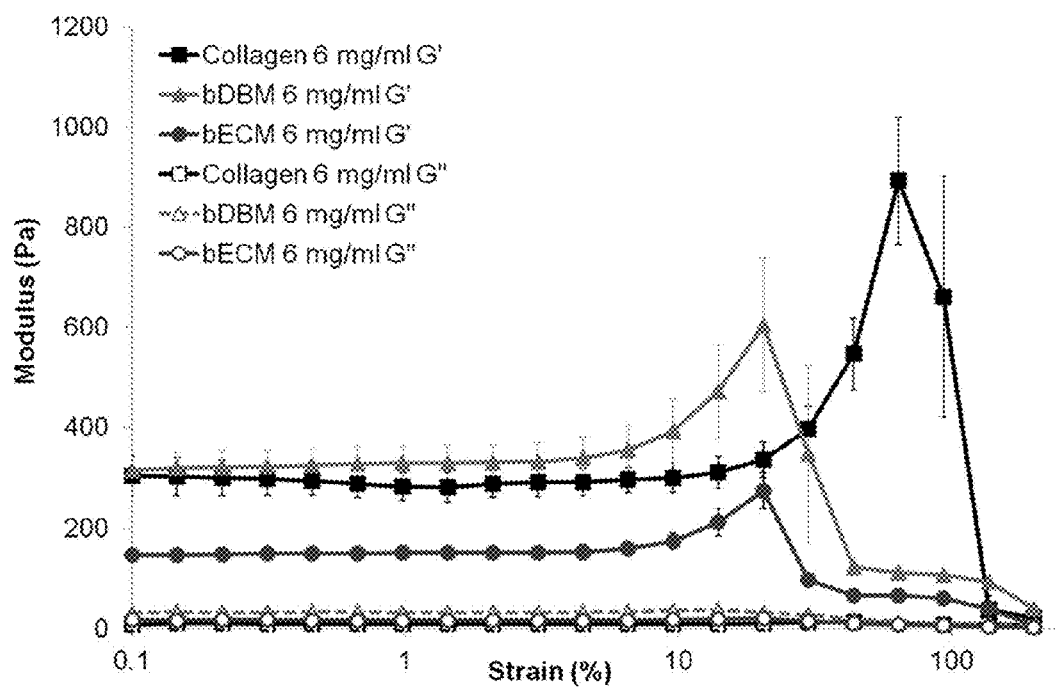

The bECM, bDBM and collagen type I hydrogels showed an increase in rate of gelation with increasing concentration, with the bECM and bDBM hydrogels having storage moduli of 32.5±3.8 and 58.7±4.3 Pa, respectively, at 3 mg ml$^{-1}$ and 143.7±7.6 and 313.0±31.2 Pa at 6 mg ml$^{-1}$ (FIGS. 4A and 4B). Immediately following the time course studies the hydrogels were subjected to an amplitude sweep of 0.1-200% strain at a constant angular frequency. As expected from the collagen content results above, all hydrogels exhibited strain stiffening behavior (FIGS. 5A and 5B), with the most marked peaks observed for collagen type I. Both the bDBM and bECM hydrogels exhibited strain stiffening at a lower strain rate than collagen type I for both concentrations. For the 6 mg ml$^{-1}$ hydrogels the maximum modulus was achieved for collagen type I at 64% strain, whereas for bDBM and bECM this occurred at 20.5% strain (FIG. 5B). The maximum storage moduli of collagen type I, bDBM and bECM 6 mg ml$^{-1}$ hydrogels were 892.7±127.1, 604.3±133.7 and 274.3±36.3 Pa, respectively (FIG. 5B). For the 3 mg ml$^{-1}$ hydrogels the maximum moduli occurred at 29.2% strain for bECM, 43.8% strain for bDBM and 93.6% strain for collagen type I (FIG. 5A). The maximum modulus of the bECM 3 mg ml$^{-1}$ hydrogel was considerably lower (202.3±14.2 Pa) than those of bDBM and collagen (507.3±76.4 and 522.3±82.5 Pa, respectively) (FIG. 5A). In the amplitude sweep for 6 mg/ml gels, all of the gels exhibit the trait expected of collagenous materials, that is, strain stiffening, but in the case of bECM and bDBM, this is observed to a lesser extent than with collagen.

5. Hydrogel Morphology

Figure 6:
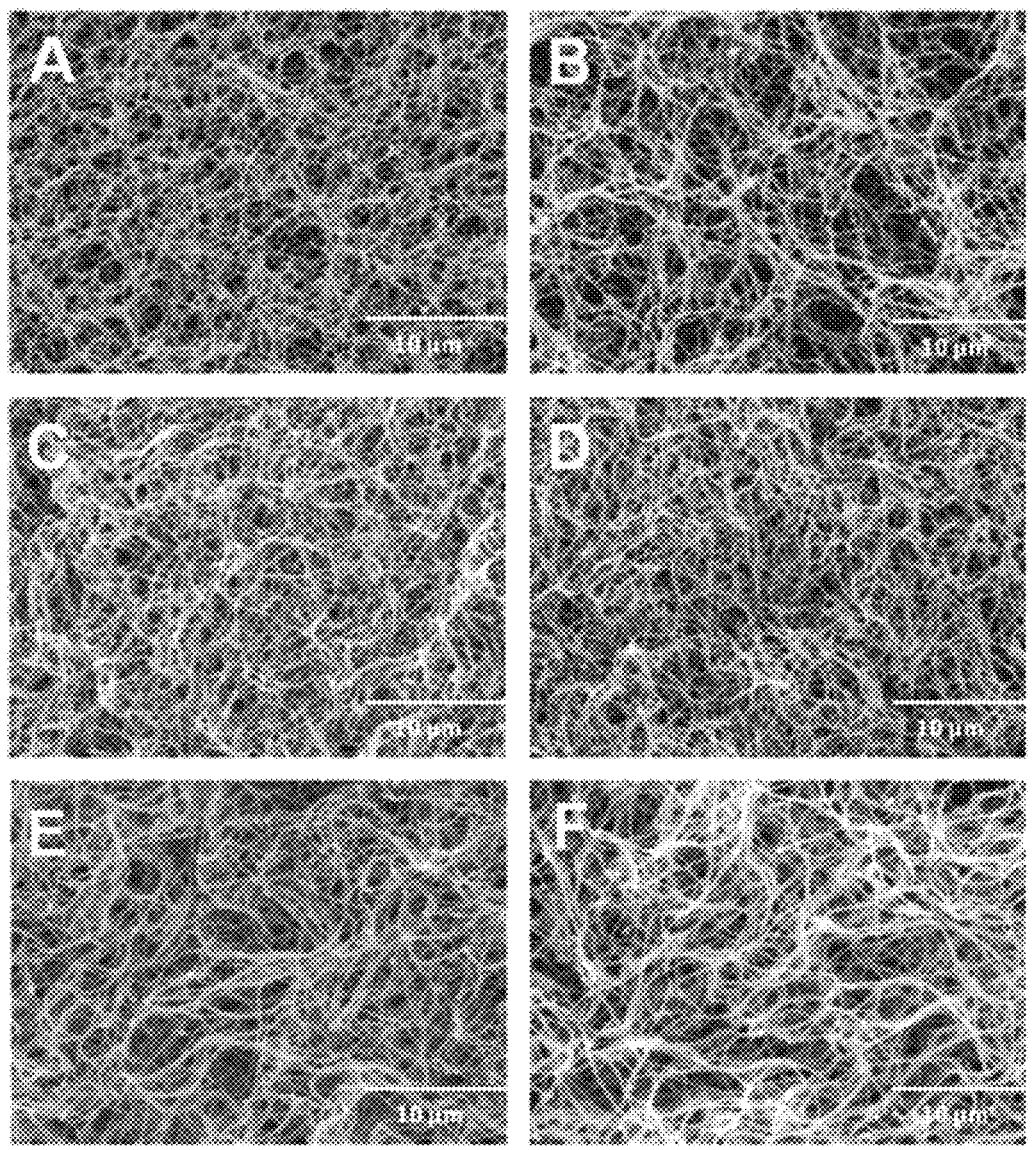
FIG. 6. Scanning electron micrographs (SEMs) of (A) bECM gel 3 mg ml$^{-1}$, (B) bECM gel 6 mg ml$^{-1}$, (C) bDBM gel 3 mg ml$^{-1}$, (D) bDBM gel 6 mg ml$^{-1}$, (E) collagen type I gel 3 mg ml$^{-1}$ and (F) collagen type I gel 6 mg ml$^{-1}$. All images 8000× magnification.

SEM of the surface of bECM, bDBM and collagen type I hydrogels showed qualitatively that both the bDBM and bECM hydrogels possessed a randomly oriented fibrillar structure, similar to collagen type I (FIG. 6). At both 3 (FIGS. 6, A, C and E) and 6 mg ml$^{-1}$ (FIGS. 6, B, D and F) all three types of hydrogels were nanofibrous with what appeared to be interconnecting pores. The organization of the collagen fibers in the bECM (FIGS. 6, A and B) and bDBM (FIGS. 6, C and D) hydrogels appeared visually similar to that of collagen type I (FIGS. 6, E and F).

Figure 7A:
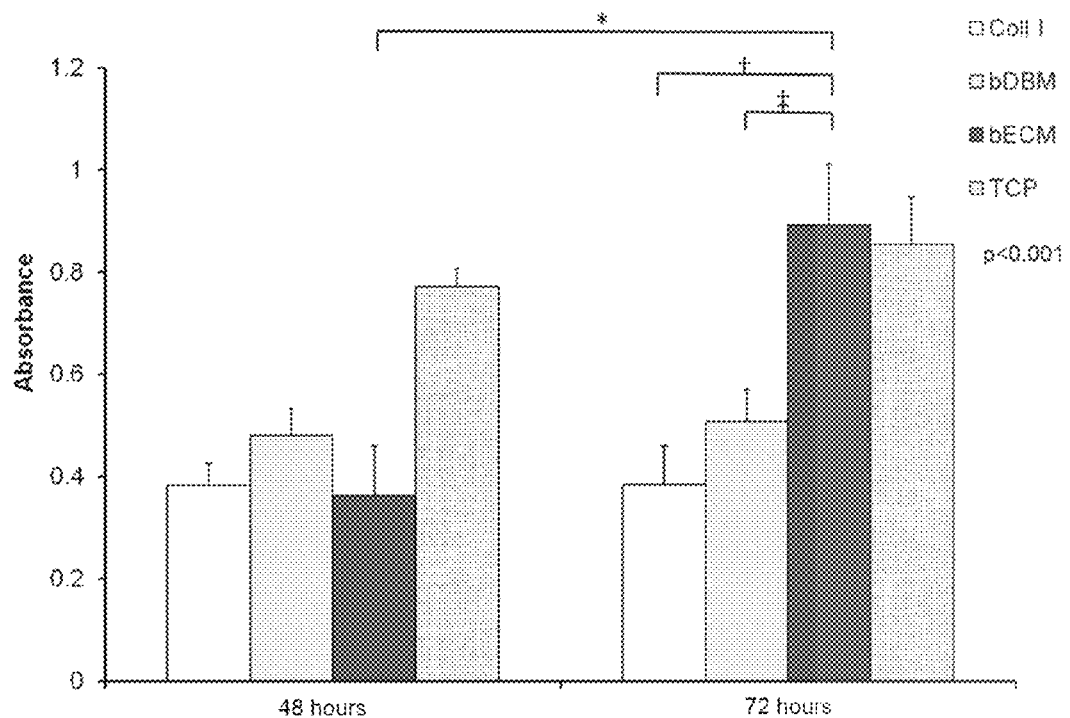
FIGS. 7A-7C. Proliferation of mPCs (mouse primary calvarial cells) on Collagen Type I, bDBM, bECM hydrogels and TCP (tissue culture plastic). *, significance between D2 and D3 for bECM; †, significance between bECM and collagen type I at the same time point; ‡, significance between bECM and bDBM at the same time point.
Figure 7B:
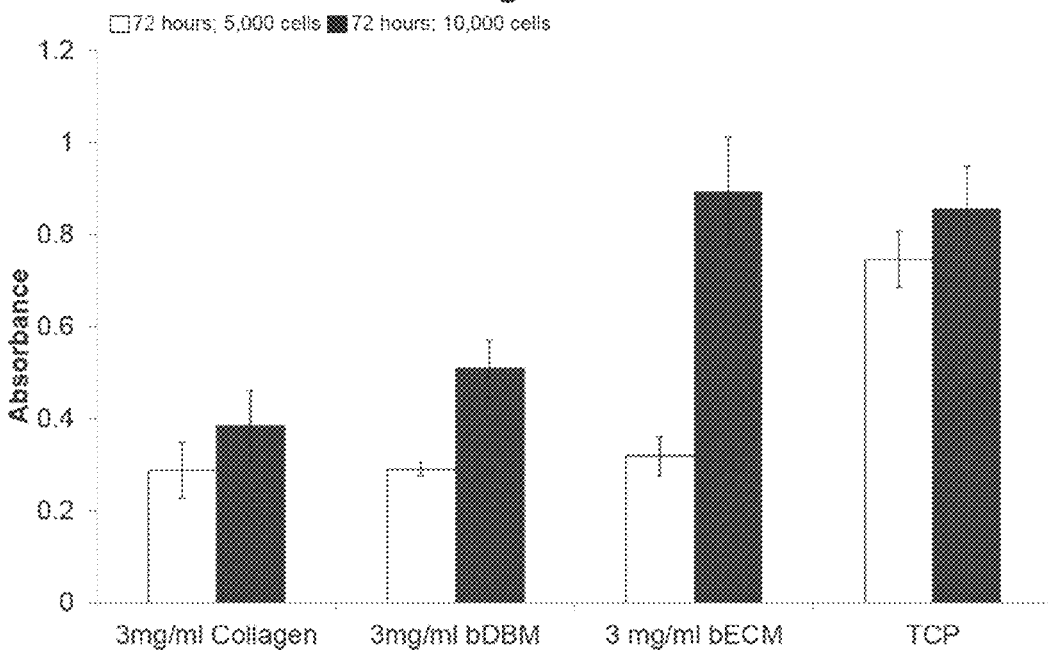
Figure 7C:
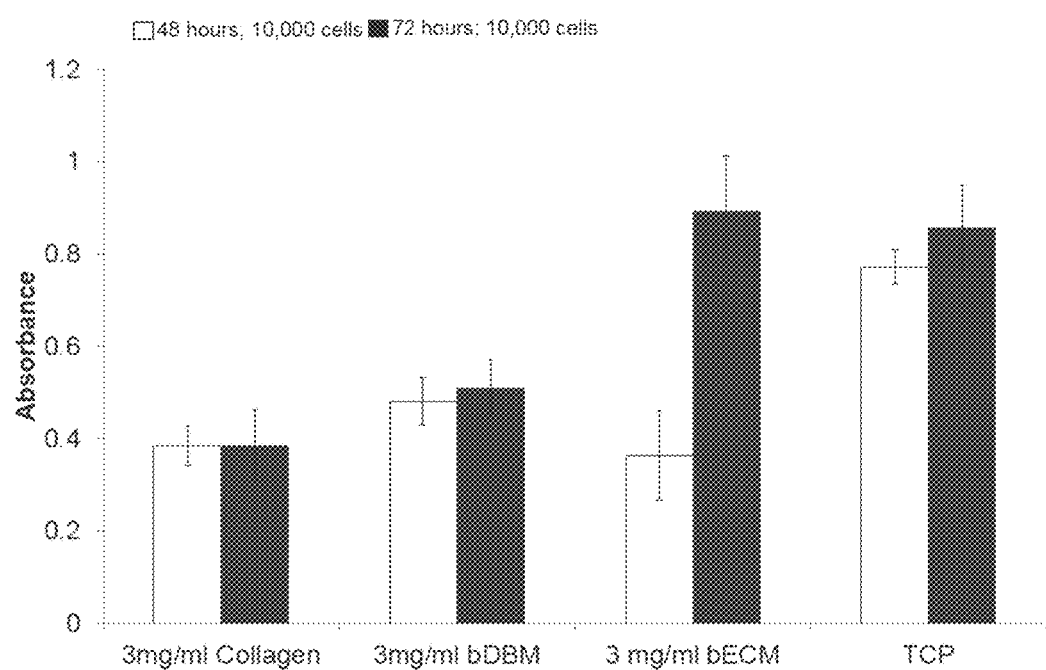

6. In Vitro Cell Culture mPCs were cultured on the surface of 3, 4, 6 and 8 mg ml$^{-1}$ bECM, bDBM and collagen type I hydrogels and TCP (tissue culture plastic). Proliferation of mPCs upon the hydrogels was assessed after 2 and 3 days. Increased proliferation of mPCs occurred between days 2 and 3 on bECM gels. For a seeding density of 10,000 cells per well, cell number was significantly greater (p<0.001) on the bECM gels compared with collagen type I and bDBM hydrogels on day 3. Similar trends were observed at all concentrations, with the results shown in FIGS. 7A-7C for 3 mg ml$^{-1}$ gels. Proliferation of an immortalized cell line on 4 mg ml$^{-1}$ hydrogels was also observed.

Discussion

DBM was prepared from bovine bone (bDBM) using an adaptation of well-documented acid extraction and lipid removal processes (Pietrzak W S, et al. *Cell Tissue Bank* 2011; 12:81-88). The bDBM was then decellularized (bECM) and both materials were solubilized and subsequently induced to form a hydrogel under physiologically relevant conditions (pH, salt concentration and temperature). The bDBM and bECM hydrogels were evaluated for structural, mechanical and in vitro cell response characteristics.

Recognition of the deleterious effects in vivo of residual cellular content upon constructive remodeling (Brown B N, et al. Macrophage phenotype and remodeling outcomes in response to biologic scaffolds with and without a cellular component. *Biomaterials* 2009; 30: 1482-91) has led to a recent definition of minimum criteria for decellularization (Crapo P M, et al. *Biomaterials* 2011; 32:3233-43). The residual DNA content of both the bDBM and bECM materials (FIG. 2C) was determined to be considerably lower than the upper limit of 50 ng dsDNA content recommended for complete decellularization (Id.). In addition, H&E staining clearly showed the qualitative absence of nuclei in the bECM sections, whereas some nuclei can be observed in the bDBM sections. This is in keeping with reported observations that DBM may retain a small percentage of cellular debris (Gruskin E, et al. *Adv Drug Deliv Rev* 2012; 64:1063-77).

The soluble collagen content of the bDBM and bECM materials was determined to be very similar (0.93±0.06 and 0.92±0.06 collagen mg initial dry weight$^{-1}$, respectively). This was expected, since bDBM (and consequently bECM) material directly derived from bone is known to be a composite of collagens (mostly type I), non-collagenous proteins and growth factors, residual calcium phosphate and retained cellular debris (Gruskin E, et al. *Adv Drug Deliv Rev* 2012; 64:1063-77). The collagenous nature of the bDBM and bECM prompted the use of collagen type I as a comparator material in the evaluation of the structural, mechanical and in vitro cell response characteristics. The in vitro self-assembly of collagen monomers into fibrils has been well studied turbidimetrically (Wood G C. The formation of fibrils from collagen solutions. 2. A mechanism of collagen-fibril formation. Biochem J 1960; 75:598-605; Wood G C, et al. Keech M K. The formation of fibrils from collagen solutions. 1. The effect of experimental conditions: kinetic and electron-microscope studies. *Biochem J* 1960; 75:588-98; and Brightman A O, et al. Time-lapse confocal reflection microscopy of collagen fibrillogenesis and extracellular matrix assembly in vitro. *Biopolymers* 2000; 54:222-34), with the mechanisms of fiber network formation clearly elucidated (Y.-l. Yang, et al. Rheology and confocal reflectance microscopy as probes of mechanical properties and structure during collagen and collagen/hyaluronan self-assembly. *Biophys J* 2009; 96:1566-85). Turbidity measurements employed in this work showed that both bDBM and bECM hydrogels exhibited sigmoidal gelation kinetics consistent with a nucleation and growth mechanism. Although the components responsible for gelation are unknown, the high soluble collagen content of the material would suggest that gelation is largely due to the presence of self-assembling collagen molecules. However, the turbidimetric gelation kinetics of both bECM and bDBM hydrogels were slower than collagen type I at the same total protein concentrations. This is most likely due to the presence of glycosaminoglycans (GAGs), different types of collagen (III and IV) and other molecules which can modulate collagen self-assembly. It has previously been demonstrated that collagen type I and interstitial ECM (derived from porcine small intestine submucosa) possess different kinetic parameters of assembly, in particular the length of the lag phase (Brightman A O, et al. *Biopolymers* 2000; 54:222-34). A decrease in turbidimetric absorbance and change in gelation kinetics of collagen type I when mixed with GAGs has also been observed, although the precise rationale for these changes has not been described (Id.). Nonetheless, these findings suggest that the gelation behavior of the bDBM and bECM hydrogels results from complex interactions between the different components retained in the materials rather than being purely dictated by collagen self-assembly.

A complex gelation behavior of the bDBM and bECM hydrogels was also indicated by rheological assessments. Although the gelation kinetics followed a sigmoidal shape, the storage moduli of both bDBM and bECM continued to increase throughout the experimental period; two phase gelation occurred at both hydrogel concentrations. As reported above, this rheological behavior is likely due to the presence of other molecules, such as GAGs, which have been shown to directly affect gel mechanical properties (Stuart K, et al. Influence of chondroitin sulfate on collagen gel structure and mechanical properties at physiologically relevant levels. *Biopolymers* 2008; 89:841-51). A similar outcome was reported for a hydrogel derived from urinary bladder matrix (UBM) (Freytes D O, et al. Preparation and rheological characterization of a gel form of the porcine urinary bladder matrix. *Biomaterials* 2008; 29:1630-7).

Although the storage modulus of the 6 mg ml$^{-1}$ bECM hydrogel (143.7±7.6 Pa) was similar to that recently reported for a hydrogel derived from decellularized dermal ECM (Wolf M T, et al. A hydrogel derived from decellularized dermal extracellular matrix. *Biomaterials* 2012; 33:7028-38), the bECM gels had significantly lower storage moduli than the bDBM or collagen type I hydrogels at both concentrations. The decellularization process discussed herein comprised the use of an enzymatic agent (trypsin) combined with a chelating agent (EDTA). Whilst trypsin is effective in the removal of cell nuclei even from dense tissues (Crapo P M, et al. *Biomaterials* 2011; 32:3233-43), cleavage of proteins such as collagen and elastin and consequent ECM disruption can occur, and this is correlated with changes in the mechanical properties (Yang M, et al. Favorable effects of the detergent and enzyme extraction method for preparing decellularized bovine pericardium scaffold for tissue engineered heart valves. *J Biomed Mater Res B Appl Biomater* 2009; 91:354-61). This effect is also evident in the strain stiffening behavior, where the maximum modulus of the bECM hydrogel was significantly lower than that of bDBM or collagen type I at both concentrations. The maximum modulus for bECM also occurred at a lower strain rate, indicating possible disruption of the hydrogel structure.

Biological scaffolds prepared from decellularized tissue have been shown to promote and facilitate constructive tissue remodeling in pre-clinical studies (Valentin J E, et al. Functional skeletal muscle formation with a biologic scaffold. *Biomaterials* 2010; 31:7475-84 and Reing J E, et al. *Biomaterials* 2010; 31:8626-33). Whilst the mechanisms of this phenomenon are not fully elucidated (Wolf M T, et al. A hydrogel derived from decellularized dermal extracellular matrix. *Biomaterials* 2012; 33:7028-38), modulation of the host immune response, recruitment of endogenous stem and progenitor cells and complete scaffold degradation play important roles. Degradation of intact ECM promotes the release of matricryptic molecules that possess bioactive properties, including chemoattractant effects and antimicrobial activity (Beattie A J, et al. Chemoattraction of progenitor cells by remodeling extracellular matrix scaffolds. *Tissue Eng Part A* 2009; 15:1119-25). Additionally, molecules released from in vitro pepsin-degraded and solubilized ECM scaffolds have been shown to affect the timing and nature of recruitment and proliferation of appropriate cell types (Reing J E, et al. Degradation products of extracellular matrix affect cell migration and proliferation. *Tissue Eng Part A* 2009; 15:605-14). In the present work we assessed the mitogenic capacity of the bECM and bDBM hydrogels, using calvarial cells, a relevant cell type for bone. The in vitro pepsin-digested and solubilized bECM hydrogel induced a higher proliferation rate compared with the similarly treated bDBM hydrogel or collagen, with cell numbers significantly greater (p<0.001) on the bECM hydrogels on day 3. DeQuach et al. (Injectable skeletal muscle matrix hydrogel promotes neovascularization and muscle cell infiltration in a hindlimb ischemia model. *Eur Cell Mater* 2012; 23:400-12) recently reported a similar increased proliferative effect of the degradation products of a skeletal muscle ECM hydrogel upon smooth muscle cells and skeletal myoblasts.

Interestingly, the proliferation of mPCs was not only significantly increased compared with collagen but also to the pepsin-digested and solubilized bDBM hydrogel. We postulate that the presence of cellular debris in the bDBM material may interfere with the activity of matricryptic molecules. Recent studies of host remodeling outcomes in response to biological scaffolds with and without cellular components may provide insights into this. Rapid degradation of acellular scaffolds was followed by replacement with site-appropriate functional host tissue, whereas the presence of cellular remnants shifted the macrophage polarization profile to predominantly M1, pro-inflammatory phenotype, and was associated with deposition of dense connective tissue (Brown B N, et al. *Biomaterials* 2009; 30: 1482-91). This poor remodeling outcome observed for cellular content in vivo may also be potentially caused by reduced proliferative capacity in vitro.

Cellular content may also be associated with the presence of the cell surface a-Gal epitope (galactose-a1,3-galactosyl-b1,4-N-acetyl glucosamine) (Badylak S F, et al. Immune response to biologic scaffold materials. *Semin Immunol* 2008; 20:109-16). The a-Gal epitope is naturally produced on glycolipids and glycoproteins in non-primate mammals, including pigs and cows (Galili U. The [alpha]-gal epitope and the anti-Gal antibody in xenotransplantation and in cancer immunotherapy. *Immunol Cell Biol* 2005; 83:674-86). However, it is absent in humans and instead a natural antibody, the anti-Gal antibody is produced. During transplantation of xenografts from pigs to humans anti-Gal antibody binds to the a-Gal epitope causing graft rejection. The role of a-Gal in modulating immune responses to xenogeneic ECM is more ambiguous. ECM materials derived from porcine small intestine submucosa contain a-Gal epitopes. In studies in both mice (Raeder R H, et al. Natural antigalactose a1,3 galactose antibodies delay, but do not prevent the acceptance of extracellular matrix xenografts. *Transpl Immunol* 2002; 10:15-24) and non-human primates (Daly K A, et al. Effect of the aGal epitope on the response to small intestinal submucosa extracellular matrix in a nonhuman primate model. *Tissue Eng Part A* 2009; 15: 3877-88) the presence of a-Gal did not adversely affect the immune and remodeling response to SIS ECM implants. More recently decellularized bovine anterior cruciate ligament (ACL) tissues were treated with a-galactosidase to remove a-Gal epitopes (Yoshida R, et al. Decellularization of bovine anterior cruciate ligament tissues minimizes immunogenic reactions to alpha-gal epitopes by human peripheral blood mononuclear cells. *Knee* 2012; 19:672-5).

No significant difference was seen between a-galactosidase-treated and decellularized bovine ACLs, which suggests that the decellularization process itself may have removed a-Gal epitopes (Id.) and that the lower number of remaining a-Gal epitopes is insufficient to cause an adverse host response. The mechanical environment of the substrate significantly affects in vitro cell behavior and thus the bECM and bDBM hydrogel structure and mechanical properties may also influence the cell response. A recent study characterized the cell infiltration and contraction of a porcine-derived dermal ECM hydrogel compared with a UBM hydrogel (Wolf M T, et al. *Biomaterials* 2012; 33:7028-38). UBM hydrogels possess a lower storage modulus and larger pore size and are thus more readily infiltrated by fibroblasts at the same ECM concentration. The bECM hydrogels studied in this work possess lower moduli than both the collagen and bDBM hydrogels, and this may have contributed to the in vitro cell response. However, fibroblast proliferation has also been shown to increase with increased collagen hydrogel stiffness (Hadjipanayi E, et al. Close dependence of fibroblast proliferation on collagen scaffold matrix stiffness. *J Tissue Eng Regen Med* 2009; 3:77-84). It is thus logical to consider that the cellular responses to bECM, bDBM and collagen hydrogels represent the overall effect of hydrogel structure, mechanical properties, constitutive molecules and the biological activity of degradation products.

The objectives of this study were to apply a stringent decellularization process to DBM, prepared from bovine bone, and to characterize the structure and composition of the bDBM and resulting bECM materials. To our knowledge this is the first time that an acellular matrix material has been produced from demineralized bone. Additionally, we have produced hydrogel forms of bDBM and bECM that possess distinct structural, mechanical and biological characteristics. Rheological characterization demonstrated that the rheological properties varied as a function of hydrogel concentration, thus ensuring that the properties of the hydrogels can be tailored for specific applications. The long-term objective of this work is to develop a gel form of DBM/ECM biological material that retains osteoconductivity and osteoinductivity. We have described the first steps towards this goal through the development of tissue-specific hydrogel scaffolds.

CONCLUSION

Bone graft substitutes, such as DBM, are usually incorporated within a carrier liquid. However, carrier liquids have been implicated in unreliable clinical delivery, including issues relating to inflammation and differences in osteogenic activity. Demineralized and decellularized bone matrices, prepared from bovine bone, can be solubilized and induced to form hydrogels. These bDBM and bECM hydrogels have distinct structural, mechanical and biological properties and have the potential for clinical delivery without the inclusion of a carrier. The biological properties of the bECM material suggest that the constituent molecules released during in vitro scaffold degradation enhance cell proliferation.

Having described this invention above, it will be understood to those of ordinary skill in the art that the same can be performed within a wide and equivalent range of conditions, formulations and other parameters without affecting the scope of the invention or any embodiment thereof.

We claim:

1. A method of preparing a bone-derived extracellular matrix (ECM) composition, comprising: (a) demineralizing bone with an acid to produce a demineralized bone matrix; (b) delipidizing the demineralized bone matrix; (c) digesting the demineralized bone matrix with trypsin and, a chelating agent, to produce decellularized, demineralized bone matrix; (d) digesting the decellularized, demineralized bone matrix with an acid protease to produce a collagenous, solubilized, bone-derived ECM composition, and (e) adjusting the pH of the solubilized, bone-derived ECM composition to between 7 and 8 to produce a neutralized pre-gel that forms a gel at 37° C.

2. The method of claim 1, wherein the bone is comminuted prior to demineralization.

3. The method of claim 1, in which the bone is cancellous bone.

4. The method of claim 1, in which the bone is demineralized in an inorganic and/or organic acid selected from the group consisting of hydrochloric acid, nitric acid, phosphoric acid, sulfuric acid, boric acid, hydrofluoric acid, hydrobromic acid, perchloric acid, acetic acid, lactic acid, formic acid, citric acid, succinic acid, oxalic acid, uric acid and a combination of any of the preceding.

5. The method of claim 1, in which the bone is demineralized with both of an acid and a chelating agent.

6. The method of claim 1, in which the DNA content of the decellularized, demineralized bone matrix is less than 50 ng per mg of the decellularized, demineralized bone matrix.

7. The method of claim 1, further comprising gelling the neutralized pre-gel at a temperature ranging from 25° C. to 42° C., thereby producing a bone-derived ECM gel.

8. The method of claim 1, further comprising washing the product of any step with an aqueous wash solution such as water, PBS, cell culture medium or saline, and subsequently freezing or drying the product of that step.

9. The method of claim 1, wherein the method comprises:
(a) demineralizing bone with hydrochloric acid and EDTA to produce a demineralized bone matrix;
(b) delipidizing the demineralized bone matrix with methanol and chloroform;
(c) digesting the demineralized bone matrix with trypsin and EDTA to produce decellularized, demineralized bone matrix;
(d) washing the decellularized, demineralized bone matrix;
(e) digesting the decellularized, demineralized bone matrix with pepsin and hydrochloric acid to produce a collagenous, solubilized, bone-derived ECM composition; and
(f) adjusting the pH of the solubilized, bone-derived ECM composition to between 7 and 8 to produce a neutralized pre-gel that forms a gel at 37° C.

10. The method of claim 1, wherein the method consists essentially of:
(a) demineralizing bone with an acid to produce a demineralized bone matrix;
(b) delipidizing the demineralized bone matrix;

(c) digesting the demineralized bone matrix with trypsin and EDTA, to produce decellularized, demineralized bone matrix;
(d) washing the decellularized, demineralized bone matrix;
(e) digesting the decellularized, demineralized bone matrix with an acid protease to produce a collagenous, solubilized, bone-derived ECM composition; and
(f) adjusting the pH of the solubilized, bone-derived ECM composition to between 7 and 8 to produce a neutralized pre-gel that forms a gel at 37° C.

* * * * *

UNITED STATES PATENT AND TRADEMARK OFFICE
CERTIFICATE OF CORRECTION

PATENT NO. : 9,861,662 B2  
APPLICATION NO. : 14/323475  
DATED : January 9, 2018  
INVENTOR(S) : Stephen F. Badylak et al.

Page 1 of 1

It is certified that error appears in the above-identified patent and that said Letters Patent is hereby corrected as shown below:

In the Claims

Column 22, Line 15, Claim 1 delete "and," and insert -- and --

Signed and Sealed this  
Third Day of April, 2018

Andrei Iancu  
*Director of the United States Patent and Trademark Office*